US007202280B2

(12) United States Patent
Räsänen et al.

(10) Patent No.: US 7,202,280 B2
(45) Date of Patent: Apr. 10, 2007

(54) METHODS FOR THE TREATMENT AND PREVENTION OF PANCREATITIS AND FOR INDUCTION OF LIVER REGENERATION

(76) Inventors: Tiina-Liisa Räsänen, Holstilantie 25, Syvanniemi (FI) 71570; Leena Alhonen, Nuottapolku 15, Vuorela (FI) 70910; Riitta Sinervirta, Jokirannantie 12, Syvänniemi (FI) 71570; Tuomo Keinänen, Myllärintie 61 B 19, Kuopio (FI) 70780; Karl-Heinz Herzig, Ruotsinrinne 20, Kuopio (FI) 70820; Alex Radii Khomutov, Lusinovskaya St., 68, Apt. 447, Moscow (RU) 113162; Jouko Vepsäläinen, Korpitie 10, Kuopio (FI) 70780; Juhani Jänne, Nuottapolku 15, Vuorela (FI) 70910

( * ) Notice: Subject to any disclaimer, the term of this patent is extended or adjusted under 35 U.S.C. 154(b) by 347 days.

(21) Appl. No.: 10/731,626

(22) Filed: Dec. 9, 2003

(65) Prior Publication Data

US 2004/0180968 A1     Sep. 16, 2004

Related U.S. Application Data

(60) Provisional application No. 60/431,958, filed on Dec. 9, 2002.

(51) Int. Cl.
*A61K 31/13* (2006.01)
(52) U.S. Cl. .................................. 514/674; 514/673
(58) Field of Classification Search ................ 514/674, 514/673
See application file for complete search history.

(56) References Cited

U.S. PATENT DOCUMENTS

| 4,330,559 | A | * | 5/1982 | Bey et al. | 514/564 |
| 5,171,754 | A | * | 12/1992 | Lau | 514/666 |
| 5,242,947 | A | * | 9/1993 | Cherksey et al. | 514/628 |
| 5,254,572 | A | * | 10/1993 | Serfontein | 514/345 |
| 5,344,846 | A | * | 9/1994 | Jakus et al. | 514/634 |
| 5,462,970 | A | * | 10/1995 | Bergeron et al. | 514/654 |
| 5,498,522 | A | * | 3/1996 | Porter | 435/6 |
| 5,516,807 | A | * | 5/1996 | Hupe et al. | 514/673 |
| 5,541,230 | A | * | 7/1996 | Basu et al. | 514/642 |
| 6,060,471 | A | * | 5/2000 | Styczynski et al. | 514/248 |
| 6,342,534 | B1 | * | 1/2002 | Bergeron, Jr. | 514/673 |
| 7,030,126 | B2 | * | 4/2006 | Ramesh et al. | 514/256 |
| 2003/0143713 | A1 | * | 7/2003 | Aghajari et al. | 435/200 |

FOREIGN PATENT DOCUMENTS

WO     WO 200147528 A2 *    7/2001

OTHER PUBLICATIONS ("Pancreatitis: Advances in Pathobiology, Diagnosis and Treatment", Barbu, S.T., Symposium Report, Oct. 14-15, 2004.*
"Chronic Pancreatitis", www.patient.co.uk, 2004.*
"Hereditary Pancreatitis", www. pancreasfoundation.org, 2004.*
Alhonen, L., et al., "Polyamines are required for the initiation of rat liver regeneration," *Biochem. J.*, 2002, 362, 149-153.
Alhonen, L., et al., "Activation of polyamine catabolism in transgenic rats induces acute pancreatitis," *J. Proc. Natl. Acad. Sci. USA*, Jul. 18, 2000, 97(15), 8290-8295.
Bernacki, R.J., et al., "Antitumor activity of N,N'-Bis(ethyl)spermine homologues against human MALME-3 melanoma xenografts," *Cancer Res.*, May 1, 1992, 52, 2424-2430.
Bernacki, R.J., et al., "Preclinical antitumor efficacy of the polyamine analogue $N^1$'$N^{11}$-diethylnorspermine administered by multiple injection or continuous infusion," *Clin. Cancer Res.*, Aug. 1995, 1, 847-848.
Bolkenius, F.N., et al., "Specific inhibition of polyamine oxidase in vivo is a method for the elucidation of its physiological role," *Biochim. Biophys. Acta*, 1985, 838, 69-76.
Casero, R.A., et al., "Spermidine/spermine N1-acetyltransferase—the turning point in polyamine metabolism," *FASEB J.*, 1993, 7, 653-661.
Greene, T.W., et al., P.G.M., Protective Groups in Organic Synthesis, 3rd Ed., *Wiley & Sons*, 1999.
Hakovirta, H., et al., "Polyamines and regualtion of spermatogenesis: selective stimulation of late spermatogonia in transgenic mice overexpressing the human ornithine decarboxylase gene," *Mol. Endocrinol.*, 1993, 7, 1430-1436.
Halmekytö, M., et al., "Transgenic mice over-producing putrescine in their tissues do not convert the diamine into higher polyamines," *Biochem. J.*, 1993, 291, 505-508.
Halmekytö, M., et al., "Transgenic mice aberrantly expressing human ornithine decarboxylase gene," *J. Biol. Chem.*, Oct. 15, 1991, 266(29), 19746-19751.
Higgins, G.H., et al., "Experimental pathology of the liver," *Arch. of Pathol.*, Jan. 20, 1931, 12, 186-202.
Hölttä, E., "Oxidation of spermidine and spermine in rat liver: purification and properties of polyamine oxidase," *Biochemistry*, 1977, 16(1), 91-100.
Hyvönen, T., et al., "Monitoring of the uptake and metabolism of aminooxy analogues of polyamines in cultured cells by high-performance liquid chromatography," *J. of Chromatogr.*, 1992, 574, 17-21.
Imrie, C.W., et al., "A prospective study of acute pancreatitis," *Br. J. Surg.*, 1975, 62, 490-494.
Jacobs, M.L., et al., "Acute pancreatitis: Analysis of factors influencing survival," *Ann. Surg.*, 1977, 185, 43-51.
Jänne, J., et al., "Polyamines: from molecular biology to clinical applications," *Ann. Of Med.*, 1991, 23, 241-259.

(Continued)

*Primary Examiner*—Brian Kwon
(74) *Attorney, Agent, or Firm*—Arent Fox LLP

(57) ABSTRACT

Novel methods for treating and preventing acute and/or chronic pancreatitis are described. Additionally, novel methods for inducing liver regeneration are described. The methods may comprise administering to a patient an effective amount of a metabolically stable analogue of spermidine and/or spermine. Preferred compounds for use in the methods may include 1-methylspermidine, 1-methylspermine and 1,12-dimethylspermine.

14 Claims, 10 Drawing Sheets

OTHER PUBLICATIONS

Jänne, J., et al., "On the purification of L-ornithine decarboxylase from rat prostate and effects of thiol compounds on the enzyme," *J. Biol. Chem.*, Mar. 25, 1971, 246(6), 1725-1732.

Khomutov, A.R., et al., "Synthesis of hydroxylamine analogues of polyamines," *Tetrahedron*, 1996, 52(43), 13751-13766.

Kumazawa, T., et al., "A radioisotopic assay for polyamine oxidase," *Anal Biochem*, 1990, 188, 105-108.

Lakanen, J.R., et al., "α-Methyl polyamines: metabolically stable spermidine and spermine mimics capable of supporting growth in cells depleted of polyamines," *J. Med. Chem.*, 1992, 35, 724-734.

Leach, S.D., et al., "New perspectives on acute pancreatitis," *Scan J. Gastroenterol*, 1992, 27 (*Suppl. 192*), 29-38.

Lukkarinen, J., et al., "Transgenic rats as models for studying the role of ornithine decarboxylase expression in permanent middle cerebral artery occlusion," *Stroke*, 1997, 28, 639-645.

Nagarajan, S., et al., "Studies of non-metabolizable polyamines that support growth of SV-3T3 cells depleted of natural polyamines by exposure to α- difluoromethylornithine," *Biochem. J.*, 1988, 254, 373-378.

Nagarajan, S., et al., "Chemistry of naturally occurring polyamines. 10.[1] Nonmetabolizable derivatives of spermine and spermidine," *J. Org. Chem.*, 1986, 51, 4856-4861.

Niederau, C., et al., "Beneficial effects of cholecystokinin-receptor blockade and inhibition of proteolytic enzyme activity in experimental acute hemorrhagic pancreatitis in mice," *J. Clin. Invest.*, 1986, 78, 1056-1063.

Pietilä, M., et al., "Activation of polyamine catabolism profoundly alters tissue polyamine pools and affects hair growth and female fertility in transgenic mice overexpressing spermidine/spermine $N^1$-acetyltransferase," *J. Biol. Chem.*, Jul. 25, 1997, 272, 18746-18751.

Räsänen, T.L., et al., "A polyamine analogue prevents acute pancreatitis and restores early liver regeneration in transgenic rats with activated polyamine catabolism," *J. Biol. Chem.*, Oct. 18, 2002, 277(42), 39867-39872.

Remington's Pharmaceutical Sciences, *Mack Pub. Co.*, 1980.

Steinberg, W., et al., "Acute pancreatitis," *N. Eng. J. Med.*, Apr. 28, 1994, 330, 1198-1210.

Suppola, S., et al., "Overexpression of spermidine/spermine $N^1$-acetyltransferase under the control of mouse metallothionein 1 promoter in transgenic mice: evidence for a striking post-transcriptional regulation of transgene expression by a polyamine analogue," *Biochem. J.*, 1999, 338, 311-316.

Suppola, S., et al., "Concurrent overexpression of ornithine decarboxylase and spermidine/spermine N1-acetyltransferase further accelerates the catabolism of hepatic polyamines in transgenic mice," *Biochem. J.*, 2001, 358, 343-348.

Vujcic, S., et al., "Genomic identification and biochemical characterization of the mammalian polyamine oxidase involved in polyamine back-conversion," *Biochem. J.*, 2003, 370, 19-28.

Vujcic, S., et al., "Identification and characterization of a novel flavin-containing spermine oxidase of mammalian cell origin," *Biochem. J.*, 2002, 367, 665-675.

Wang, Y., et al., "Properties of purified recombinant human polyamine oxidase, PAOh1/SMO," *Biochem. Biophys. Res. Commun.*, 2003, 304, 605-611.

Wu, T., et al., "Cloning, sequencing, and heterologous expression of the murine peroxisomal flavoprotein, N1-acetylated polyamine oxidase," *J. Biol. Chem.*, Jun. 6, 2003, 278(23), 20514-20525.

* cited by examiner

METHODS FOR THE TREATMENT AND PREVENTION OF PANCREATITIS AND FOR INDUCTION OF LIVER REGENERATION

CROSS-REFERENCE TO RELATED APPLICATIONS

This application claims benefit of U.S. Provisional Application No. 60/431,958, filed Dec. 9, 2002, the entire disclosure of which is hereby incorporated by reference herein, in its entirety.

FIELD OF THE INVENTION

The present invention relates to novel methods for the treatment and prevention of pancreatitis. The present invention also relates to novel methods for the induction of liver regeneration. More particularly, the present invention relates to novel methods for the treatment and prevention of pancreatitis and for the induction of liver regeneration by using metabolically stable polyamine compounds.

BACKGROUND OF THE INVENTION

The polyamines spermidine and spermine and their precursor putrescine are small aliphatic cations under normal physiological conditions and are intimately associated with growth and differentiation of mammalian cells, yet their exact cellular functions have not been solved (Jänne, J., Alhonen, L., and Leinonen, P. (1991) Ann. Med. 23, 241–259). In attempts to elucidate the physiological roles of the polyamines, a number of transgenic mouse and rat lines with genetically altered polyamine metabolism have been generated. The activation of polyamine biosynthesis through an overexpression of ornithine decarboxylase (ODC) brings about many interesting phenotypic changes, such as male infertility (Halmekytö, M., Hyttinen, J.-M., Sinervirta, R., Utriainen, M., Myöhänen, S., Voipio, H.-M., Wahlfors, J., Sydjänen, S., Syjänen, K., Alhonen, L., and Jänne, J. (1991) J. Biol. Chem. 266, 19746–19751; Hakovirta, H., Keiski, A., Toppari, J., Halmekytö, M., Alhonen, L., Jänne, J., and Parvinen, M. (1993) Mol. Endocrinol. 7, 1430–1436), yet these studies are complicated by the fact that overexpression of ODC only increases tissue putrescine pools, as the latter diamine is not further converted to spermidine and spermine (Halmekytö, M., Alhonen, L., Alakuijala, L., and Jänne, J. (1993) Biochem. J. 291, 505–508; Suppola, S., Heikkinen, S., Parkkinen, J. J., Uusi-Oukari, M., Korhonen, V. P., Keinänen, T., Alhonen, L., and Jänne, J. (2001) Biochem J. 358, 343–348).

Much more severe distortion of tissue polyamine pools has been achieved by activation of polyamine catabolism through an overexpression of spermidine/spermine $N^1$-acetyltransferase (SSAT) in transgenic rodents. The latter enzyme catalyzes the rate-controlling reaction in the catabolism of spermidine and spermine. After being acetylated, $N^1$-acetylspermidine is converted to putrescine and $N^1$-acetylspermine to spermidine by the action of polyamine oxidase (PAO) (Casero, R. A., and Pegg, A. E. (1993) FASEB J. 7, 653–661). Overexpression of SSAT in transgenic rodents results in profound changes in tissue polyamine pools, such as massive accumulation of putrescine, appearance of $N^1$-acetylspermidine and decreases in spermidine and/or spermine pools (Pietilä, M., Alhonen, L., Halmnekytö, M., Kanter, P., Jänne, J., and Porter, C. W. (1997) J. Biol. Chem. 272, 18746–18751). The alterations in polyamine homeostasis are accompanied by bizarre phenotypic changes, such as early and permanent loss of hair, extensive wrinkling of the skin upon aging, lack of subcutaneous fat (Pietilä, M., Alhonen, L., Halmekytö, M., Kanter, P., Jänne, J., and Porter, C. W. (1997) J. Biol. Chem. 272, 18746–18751) and reduced life span (Suppola, S., Heikkinen, S., Parkkinen, J. J., Uusi-Oukari, M., Korhonen, V. P., Keinänen, T., Alhonen, L., and Jänne, J. (2001) Biochem J. 358, 343–348). Transgenic rats have been generated in which SSAT expression is driven by the heavy metal-inducible mouse metallothionein I promoter (Alhonen, L., Parkkinen, J. J., Keinänen, T., Sinervirta, R. Herzig, K.-H., and Jänne, J. Proc. Natl. Acad. Sci. U.S.A., 97, 8290–8295 (2000)). The metallothionein promoter directs the expression of SSAT mainly into liver and pancreas in a heavy metal-inducible fashion. Exposure of the transgenic rats to nontoxic doses of zinc resulted in an immense induction of SSAT activity in the pancreas, a profound depletion of pancreatic spermidine and spermine pools and acute pancreatitis (Alhonen, L., Parkkinen, J. J., Keinänen, T., Sinervirta, R., Herzig, K. H., and Jänne, J. (2000) Proc. Natl. Acad. Sci. U.S.A. 97, 8290–8295). The fact that pancreatitis could not be prevented by inhibition of PAO, which generates hydrogen peroxide and a reactive aldehydes, suggested that the organ inflammation was causally related to the profound depletion of spermidine and spermine (Alhonen, L., Parkkinen, J. J., Keinänen, T., Sinervirta, R., Herzig, K. H., and Jänne, J. (2000) Proc. Natl. Acad. Sci. U.S.A. 97, 8290–8295).

Acute pancreatitis is a common clinical problem which remains evasive of specific therapy (Leach S D, Gorelick S, Modlin I M: New perspectives on acute pancreatitis. Scan J Gastroenterol 27 Suppl 192:29–38, 1992). Each year more than 210,000 admissions to U.S. hospitals are caused by acute pancreatitis while another 150,000 are due to chronic pancreatitis. Pancreatitis is most often caused by alcoholism or biliary tract disease. Less commonly, it is associated with hyperlipemia, hyperparathyroidism, abdominal trauma, vasculitis or uremia. The average length of hospitalization for the acute disease is 12.4 days, with a significant number of patients staying much longer because of associated complications.

The overall mortality for acute pancreatitis varies between 6 and 18% and can raise as high as 50% in the more fulminant form (Steinberg W, Tenner S: Acute pancreatitis. N Eng J Med 330:1198–1220, 1994; Imrie C W, Whyte A S: A prospective study of acute pancreatitis. Br J Surg 62:490–494, 1975; Jacobs M L, Daggett W M, et al: Acute pancreatitis: Analysis of factors influencing survival. Ann Surg 185:43–51, 1977). Interestingly, the prognosis for this disease appears more dependent upon its systemic manifestations and complications than upon the severity of the local pancreatic inflammation (Imrie and Whyte, 1975; Jacobs et al., 1977). In fact, as many as 60% of deaths from acute pancreatitis which occur within one week of onset can be attributed to adult respiratory distress syndrome (ARDS), which cannot be distinguished from sepsis-associated ARDS (Steinberg and Tenner, 1994; Jacobs et al., 1977).

Chronic pancreatitis develops in those patients who continue to drink after their first bout of pancreatitis or those with gallstone pancreatitis for unknown reasons. The recurrent bouts of acute pancreatitis subsequently become less severe and less life threatening. The typical patient with chronic pancreatitis, however, is admitted to the hospital approximately one to two times per year for the rest of their lives. These patients have a decreased life span when compared to their peers (Imrie and Whyte, 1975; Steinberg and Tenner, 1994). Despite the less severe course of the disease, it causes chronic debilitating pain and numerous hospitalizations and loss of productivity. These patients often have chronic pain to such a degree that they become dependent upon narcotics or require operative intervention in attempts to remove or ablate some of the chronically inflamed pancreas.

Chronic ethanol abuse is one of the most common cause of acute and chronic pancreatitis in the West, yet the pathophysiology of this disease remains poorly understood (Steinberg and Tenner, 1994). There are few medical therapies or pharmacologic agents currently available which have been shown to decrease the severity, duration, complication rate, or mortality for this common disease. Care for these patients, regardless of the etiology, remains primarily supportive, with attention directed towards maintaining an adequate circulating blood volume, supporting renal and respiratory systems, and providing adequate nutrition. This lack of specific therapy has prompted a great number of prospective trials during the past two decades in hopes of finding some way to decrease the progression and severity of this disease. To date, specific therapy remains unknown and a search for new, more effective modalities is necessary.

Current specific treatments in use and/or proposed for pancreatitis comprise, for example, using bradykinin-antagonists, using IL-11, IL-1 block such as Interleukin-1 converting enzyme (ICE) antagonist, and insulin sensitizers.

When transgenic rats in which SSAT expression is driven by the mouse metallothionein I promoter were subsequently subjected to partial hepatectomy, a striking stimulation of SSAT activity was observed that was associated with a rapid depletion of the hepatic spermidine pool at 24 h after operation (Alhonen, L., Räsänen, T. L., Sinervirta, R., Parkkinen, J. J., Korhonen, V. P., Pietilä, M., and Jänne, J. (2002) *Biochem. J.* 362, 149–153). Under these conditions, the transgenic rats failed to initiate liver regeneration, as judged by lack of proliferative activity and organ weight gain. The regeneration was restored only after spermidine concentration returned to the preoperative level, presumably due to enhanced ODC activity (Alhonen, L., Räsänen, T. L., Sinervirta, R., Parkkinen, J. J., Korhonen, V. P., Pietilä, M., and Jänne, J. (2002) *Biochem. J.* 362, 149–153).

Accordingly, the present invention is directed, among other important ends, to novel methods for the treatment and prevention of pancreatitis using polyamines and/or polyamine analogues, and to methods of stimulating liver regeneration using polyamines and/or polyamine analogues.

SUMMARY OF THE INVENTION

The present invention is directed, in part, to novel methods for the treatment and prevention of pancreatitis, and for inducing liver regeneration. Specifically, in one embodiment, there are provided novel methods for treating or preventing pancreatitis comprising administering to a patient an effective amount of a compound of formula (I):

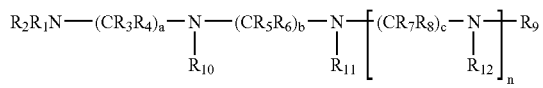

wherein:
each of a, b and c is an integer from 2 to about 6;
n is an integer 0 or 1; and
each of $R_1$, $R_2$, $R_3$, $R_4$, $R_5$, $R_6$, $R_7$, $R_8$, $R_9$, $R_{10}$, $R_{11}$ and $R_{12}$ are, independently, hydrogen or alkyl of 1 to about 6 carbons;

with the proviso that when n is 0, at least one of $R_3$, $R_4$, $R_5$, and $R_6$ is alkyl of 1 to about 6 carbons, and when n is 1, at least one of $R_3$, $R_4$, $R_5$, $R_6$, $R_7$ and $R_8$ is alkyl of 1 to about 6 carbons.

Another embodiment of the invention relates to a method of treating or preventing pancreatitis comprising administering to a patient an effective amount of a metabolically stable analogue of spermidine.

Another embodiment of the invention relates to a method of treating or preventing pancreatitis comprising administering to a patient an effective amount of a metabolically stable analogue of spermine.

Yet another embodiment of the invention relates to a method of inducing liver regeneration comprising administering to a patient an effective amount of a compound of formula (I):

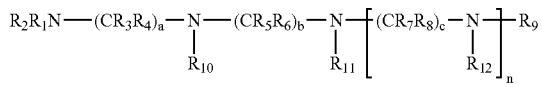

wherein:
each of a, b and c is an integer from 2 to about 6;
n is an integer 0 or 1; and
each of $R_1$, $R_2$, $R_3$, $R_4$, $R_5$, $R_6$, $R_7$, $R_8$, $R_9$, $R_{10}$, $R_{11}$ and $R_{12}$ are, independently, hydrogen or alkyl of 1 to about 6 carbons;

with the proviso that when n is 0, at least one of $R_3$, $R_4$, $R_5$, and $R_6$ is alkyl of 1 to about 6 carbons, and when n is 1, at least one of $R_3$, $R_4$, $R_5$, $R_6$, $R_7$ and $R_8$ is alkyl of 1 to about 6 carbons.

Yet another embodiment of the invention relates to a method of inducing liver regeneration comprising administering to a patient an effective amount of a metabolically stable analogue of spermidine.

Yet another embodiment of the invention relates to a method of inducing liver regeneration comprising administering to a patient an effective amount of a metabolically stable analogue of spermine.

BRIEF DESCRIPTION OF THE DRAWINGS

The application file contains at least one drawing executed in color. Copies of this patent application publication with color drawings will be provided by the Office upon request and payment of the necessary fee.

FIG. 3a shows histology of normal pancreas (no zinc induction). The animals received zinc (10 mg/kg) 24 h before sacrifice without (FIG. 3b) or with methylspermidine (50 mg/kg) either as single dose 4 h before zinc (FIG. 3c) or as two doses 20 h and 4 h before zinc (FIG. 3d).

DETAILED DESCRIPTION OF ILLUSTRATIVE EMBODIMENTS

Figure 1:
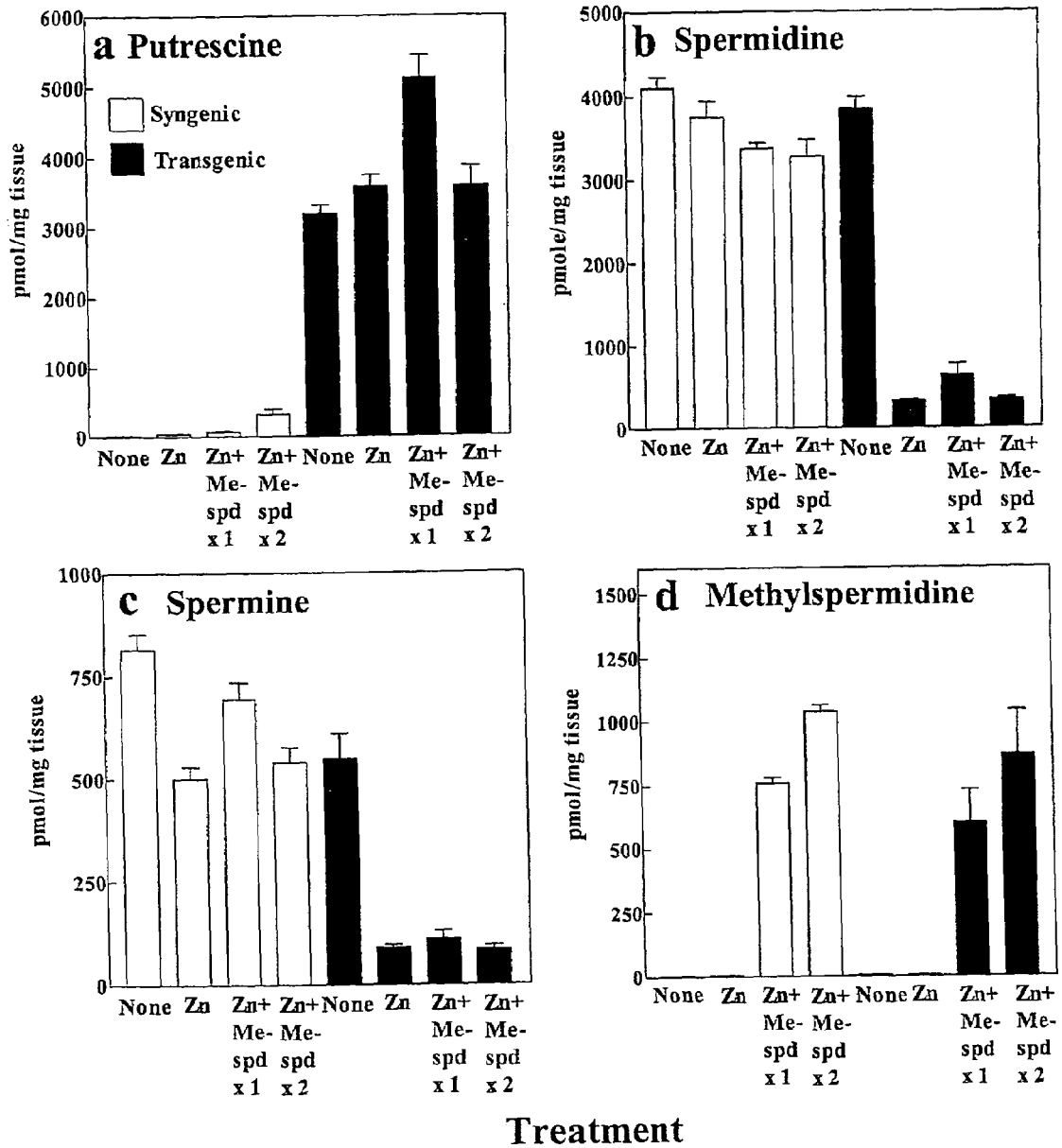
FIGS. 1a–1d. Pancreatic polyamine pools in syngenic and transgenic rats after zinc and methylspermidine. The animals received zinc (10 mg/kg) 24 h before sacrifice without or with methylspermidine (50 mg/kg) either as single dose 4 h before zinc or as two doses 20 h and 4 h before zinc. Three to five animals in each group. Me-spd, methylspermidine.

As employed above and throughout the disclosure, the following terms, unless otherwise indicated, shall be understood to have the following meanings.

"Alkyl" refers to an aliphatic hydrocarbon group which may be straight, branched or cyclic having from 1 to about 10 carbon atoms in the chain, and all combinations and subcombinations of ranges and specific numbers of carbons therein. "Branched" refers to an alkyl group in which a lower alkyl group, such as methyl, ethyl or propyl, is attached to a linear alkyl chain. Exemplary alkyl groups include methyl, ethyl, n-propyl, isopropyl, butyl, isobutyl, sec-butyl, tert-butyl, pentyl, hexyl, heptyl, octyl, nonyl and decyl.

"Effective amount" refers to an amount of a compound as described herein that may be therapeutically effective to treat or prevent the symptoms of a particular condition or disorder. Such conditions or disorders may include, but are not limited to, pathological conditions associated with pancreatitis and/or conditions in which induction of liver regeneration is sought. Such therapeutically effective activity may be achieved, for example, by contacting cells, tissues and/or receptors with compounds of the present invention.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base and zwitterions, are contemplated to be within the scope of the present invention.

In the formulas described and claimed herein, it is intended that when any symbol appears more than once in a particular formula or substituent, its meaning in each instance is independent of the other.

"Patient" refers to animals, including mammals, preferably humans.

"Metabolic" refers to having to do with chemical changes involved in the processes of growth and repair in a living organism, including the anabolic and catabolic processes.

In certain embodiments, the present invention is directed to methods for treating or preventing pancreatitis. Pancreatitis may be characterized by an inflammatory, autodigestive process of the pancreas. Different types of pancreatitis may be treated and/or prevented using the methods of the present invention. The present methods are suitable for treating and/or preventing acute as well as chronic pancreatitis. The present methods are suitable for treating and/or preventing necrotizing as well as non-necrotizing pancreatitis. "Necrotizing pancreatitis" may be characterized by cell death caused by the progressive degradative action of enzymes. "Non-necrotizing pancreatitis" may be characterized by inflammation of the pancreas that does not include significant necrosis of the pancreas.

While not intending to be bound by any theory or theories of operation, it is contemplated that pancreatitis may result from depletion of in vivo polyamines, particularly spermine and spermidine.

The methods of the present invention may also be used to induce liver regeneration. While not intending to be bound by any theory or theories of operation, it is contemplated that liver regeneration may depend on a critical in vivo concentration of polyamines, particularly spermine and spermidine.

In certain embodiments, the present invention is directed to administering to a patient an effective amount of a polyamine analogue. Polyamine analogues which may be used in embodiments of the present invention include, but are not limited to, those described in Nagarajan & Ganem, *J. Org. Chem.* (1986) 51, 4856–4861 and Nagarajan et. al *Biochem. J.* (1988) 254, 373–378, the disclosures of each of which are hereby incorporated herein by reference in their entireties. In one embodiment of the invention, the methods of the present invention involve administering to a patient an effective amount of a compound which is a metabolically stable analog of spermidine. In another embodiment of the invention, the methods of the present invention may involve administering to a patient a derivative of spermine.

The term "spermidine", as used herein, refers to the compound $H_2N$—$(CH_2)_3$—$NH(CH_2)_4$—$NH_2$. The term "metabolically stable analogue of spermidine", as used herein, refers to compounds which are structurally related to spermidine, but which are substantially not metabolized in vivo, including, but not limited to, (1-methylspermidine) $H_2N$—$CH(CH_3)$—$(CH_2)_2$—$NH(CH_2)_4$—$NH_2$. Such metabolically stable analogues may include spermidine analogues which are not substantially susceptible to enzymes that metabolize polyamines.

Thus, metabolically stable analogues of spermidine include, for example, polyamine hydrocarbon compounds (i.e., hydrocarbon compounds which contain two or more substituted or unsubstituted amino groups). Preferably, the metabolically stable analogues of spermidine are alkylated analogues of spermidine (i.e., spermidine and structurally related compounds which are substituted with one or more alkyl groups).

In preferred form, the polyamine compounds employed in the present methods have the following formula (I):

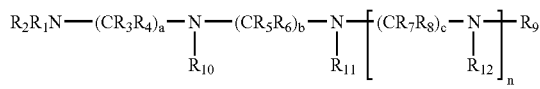

wherein:
each of a, b and c is an integer from 1 to about 6;
n is an integer 0 or 1; and
each of $R_1$, $R_2$, $R_3$, $R_4$, $R_5$, $R_6$, $R_7$, $R_8$, $R_9$, $R_{10}$, $R_{11}$ and $R_{12}$ are, independently, hydrogen or alkyl of 1 to about 6 carbons;
with the proviso that when n is 0, at least one of $R_3$, $R_4$, $R_5$, and $R_6$ is alkyl of 1 to about 6 carbons, and when n is 1, at least one of $R_3$, 4, $R_5$, $R_6$, $R_7$ and $R_8$ is alkyl of 1 to about 6 carbons.

Preferably, in the above compound of formula (I), each of a, b and c is an integer from about 2 to about 6. More preferably, a is 3, b is 4 and n is 0. More preferably, each of $R_3$, $R_4$, $R_5$, and $R_6$ is, independently, hydrogen or methyl. More preferably, the compound of formula I has the formula

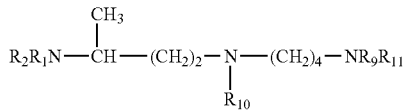

In a particularly preferred embodiment, each of $R_1$, $R_2$, $R_9$, $R_{10}$ and $R_{11}$ is hydrogen (1-methylspermidine). In certain embodiments, the compound of formula I has the formula

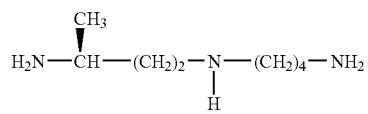

while in other embodiments, the compound of formula I has the formula

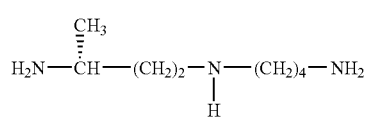

The term "spermine", as used herein, refers to the compound $H_2N$—$(CH_2)_3$—$NH(CH_2)_4$—$NH(CH_2)_3$—$NH_2$. The term "metabolically stable analogue of spermine", as used herein, refers to compounds which are structurally related to spermine that are more resistant, compared to spermine, to the action of certain enzymes that metabolize polyamines (nonlimiting examples of such enzymes include PAO and SMO), including, but not limited to, mono- and diaminooxidases that catalyze oxidative deamination of the primary amine. Examples of such spermine analogues include, without limitation, 1-methylspermine ($H_2N$—$CH(CH_3)$—$(CH_2)_2$—$NH(CH_2)_4$—$NH(CH_2)_3$—$NH_2$) and 1,12-dimethylspermine ($H_2N$—$CH(CH_3)$—$(CH_2)_2$—$NH(CH_2)_4$—$NH(CH_2)_2$—$CH(CH_3)$—$NH_2$).

Analogues of spermine which may be useful in certain embodiments of the invention include, for example, polyamine hydrocarbon compounds (i.e., hydrocarbon compounds which contain two or more substituted or unsubstituted amino groups). Preferably, the metabolically stable analogues of spermine are alkylated analogues of spermine (i.e., spermine and structurally related compounds which are substituted with one or more alkyl groups).

In an alternate embodiment, in the above compound of formula (I), a is 3, b is 4, c is 3, and n is 1. Preferably, each of $R_3$, $R_4$, $R_5$, $R_6$, $R_7$, and $R_8$ is, independently, hydrogen or methyl. More preferably, the compound of formula I has the formula

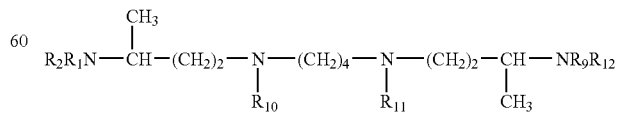

In a particularly preferred embodiment, each of $R_1$, $R_2$, $R_9$, $R_{10}$, $R_{11}$, and $R_{12}$ is hydrogen (1,12-dimethylspermine).

In an alternate embodiment, the compound of formula I has the formula

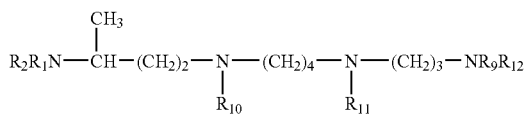

In a particularly preferred embodiment, each of $R_1$, $R_2$, $R_9$, $R_{10}$, $R_{11}$ and $R_{12}$ is hydrogen (1-methylspermine).

All numerical ranges described herein include all combinations and subcombinations of ranges and specific integers encompassed therein.

When any variable occurs more than one time in any constituent or in any formula described herein, its definition in each occurrence is independent of its definition at every other occurrence. Combinations of substituents and/or variables are permissible only if such combinations result in stable compounds.

The compounds employed in the methods of the present invention may exist in prodrug form. As used herein, the term "prodrug" is intended to include any covalently bonded carriers which release the active parent drug according to formula (I) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.), the compounds employed in the present methods may, if desired, be delivered in prodrug form. Thus, the present invention contemplates methods of delivering prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, thiol, amino, or carboxy group is bonded to any group that, when the prodrug is administered to a mammalian subject, cleaves to form a free hydroxyl, thiol, free amino, or carboxylic acid, respectively. Examples include, but are not limited to, acetoxyalkyls, acetate, formate and benzoate derivatives of alcohol, thiol, and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by methods described in Nagarajan & Ganem, *J. Org. Chem.* (1986) 51, 4856–4861 and Nagarajan et. al *Biochem. J.* (1988) 254, 373–378, the disclosures of each of which are hereby incorporated herein by reference in their entireties, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 3d. Ed., Wiley & Sons, 1999.

The compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients.

The compounds may be combined with a pharmaceutical carrier selected on the basis of the chosen route of administration and standard pharmaceutical practice as described, for example, in Remington's Pharmaceutical Sciences (Mack Pub. Co., Easton, Pa., 1980), the disclosures of which are hereby incorporated herein by reference, in their entireties.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol. The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least about 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound, and all combinations and subcombinations of ranges and specific amounts therein.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable will vary with the form of administration, the particular compound chosen and the physiological characteristics of the particular patient under treatment. Generally, small dosages may be used initially and, if necessary, increased by small increments until the desired effect under the circumstances is reached.

EXAMPLES

The invention is further demonstrated in the following examples. All of the examples are actual examples. The examples are for purposes of illustration and are not intended to limit the scope of the present invention.

Materials And Methods

Generation of Transgenic Rats and Mice and In Vivo Studies of α-methylated Polyamine Analogues.

The production of transgenic Wistar rats (UKUR30) and mice (UKU181) harboring metallothionein-SSAT fusion gene (Suppola, S., Pietilä, M., Parkkinen, J. J., Korhonen, V. P., Alhonen, L., Halmekytö, M., Porter, C. W., and Jänne, J. (1999) *Biochem. J.* 338, 311–316) has been described earlier (Alhonen, L., Parkkinen, J. J., Keinänen, T., Sinervirta, R., Herzig, K. H., and Jänne, J. (2000) *Proc. Natl. Acad. Sci. U.S.A.* 97, 8290–8295; Lukkarinen, J., Gröhn, O., Sinervirta, R., Järvinen, A., Kauppinen, R. A., Jänne, J., and Alhonen, L. (1997) *Stroke* 28, 639–645). Partial hepatectomy was carried out according to the original method of Higgins and Anderson (Higgins, G. H., and Anderson, R. M. (1931) *Arch. Pathol.* 12, 186–202). Treatments before partial hepatectomy and the determination of DNA synthesis were carried out as in (Räsänen, T. L., Alhonen, L., Sinervirta, R., Keinänen, T., Herzig, K. H., Suppola, S., Khomutov, A. R., Vepsäläinen, J., and Jänne, J. (2002) J. Biol. Chem. 277, 39867–39872). Transgenic 10 weeks old male rats were injected twice with MDL72527 (50 mg/kg i.p.) at 16-h interval to inactivate PAO according to (Bolkenius, F. N., Bey, P., and Seiler, N. (1985) Biochim. Biophys. Acta 838, 69–76) and further with α-methylspermidine, α-methylspermidine or bis-α-methylspermine twice (25 mg/kg i.p.) 2 and 8 hours after the second MDL72527 treatment. Animals not treated with the PAO inhibitor were injected with α-methylated spermine analogues or α-methyspermidine at the same time points as MDL72527 pretreated animals. The animals were sacrificed 24 h after the second MDL72527 injection and liver pieces were frozen in liquid nitrogen, homogenized in buffer (25 mM Tris-HCl pH 7.4, 0.1 mM EDTA, 1 mM DTT). An aliquot of the homogenates was used for the polyamine assays. The homogenates were centrifuged (at 13 000×g, for 30 min, at 4° C.) and the supernatants were used for the enzyme activity assays. The Institutional Animal Care and Use Committee of the University of Kuopio and by the Provincial Government approved animal experiments.

Back-conversion Studies of the α-methylated Polyamine Analogues on Liver Extracts in Vitro.

Wild-type Wistar male rats were sacrificed and livers were processed as above. All supernatants were combined and eluted at 4° C. through an Amicon Ultra-15 centrifugal filter devices (Millipore) with nominal molecular weight limit of 30 000 with high-salt (500 mM NaCl) buffer to remove the natural polyamines. The resulting eluates were desalted in the same columns with non-salt buffer three times to remove excess salt. The final eluates were pooled and the protein concentrations were determined. Experiments were carried out in triplicates where 40 μl of liver extract was used per total reaction volume of 180 μl. Reaction buffer containing 0.1 M glycine-NaOH pH 9.5 and 5 mM DTT was used to study the metabolism of the polyamines and their α-methylated analogues in 1 mM concentrations. The reactions were initiated with the studied polyamine or analogues addition and the reaction tubes incubated at 37° C. water-bath for 60 min. Five millimolar freshly distilled benzaldehyde was used to decrease the $K_m$ value and to increase the reaction velocity of PAO according to (Hölttä, E. (1977) Biochemistry 16, 91–100). The reaction mixtures were pre-incubated for 10 min with 250 μM MDL72527 to inactivate PAO before the polyamine or analogue addition. The reactions were stopped with the addition of 20 μl of 100 μM diaminohexane in 50% w/v sulphosalisylic acid.

Chemicals.

The polyamine oxidase inhibitor MDL72527 [$N^1$, $N^2$-bis (2,3-butadienyl-1,4-butanediamine] was a generous gift from Hoechst-Roussel. 1-methylspermidine (also referred to herein as 1-MeSpd, MeSpd, α-MeSpd, and methylspermidine), 1-methylspermine (also referred to herein as 1-MeSpm, MeSpm, α-MeSpm, methylspermine) and 1,12-dimethylspermine (also referred to herein as bis-α-methylspermine, Me$_2$Spm, bis-α-MeSpm, bis-methylspermine) were synthesized starting from 3-aminobutanol as described in (Khomutov, A. R., Vepsäläinen, J. J., Shvetsov, A. S., Hyvönen, T., Keinänen, T., Pustobaev, V. N., Eloranta, T. O., and Khomutov, R. M. (1996) Tetrahedron 52, 13751–13766) and administered in saline. All other chemicals were purchased from Sigma-Aldrich and Fluka. [6-$^3$H] Thymidine (specific radioactivity 18 Ci/mmole) was obtained from Perkin Elmer Life Sciences. Zinc was administered as zinc sulfate dissolved in distilled water.

Production of Recombinant Spermine Oxidase and Polyamine Oxidase Enzymes.

The E. coli expression vectors, production and purification of recombinant spermine oxidase and polyamine oxidase proteins were carried out essentially as described in (Wang Y, Murray-Stewart T, Devereux W, Hacker A, Frydman B, Woster P M, Casero R A Jr. Biochem Biophys Res Commun. 2003 May 16;304(4):605–11, Wu T, Yankovskaya V, McIntire W S. J Biol. Chem. 2003 Jun. 6;278(23): 20514–25, Vujcic S, Liang P, Diegelman P, Kramer D L, Porter C W. Biochem J. 2003 Feb. 15;370(Pt 1):19–28, Vujcic S, Diegelman P, Bacchi C J, Kramer D L, Porter C W. Biochem J. 2002 Nov. 1;367(Pt 3):665–75). Purified enzymes were used for the stability testing of α-methylated polyamine analogs as described above by replacing the liver extract in the reaction mixture with pure enzymes.

Analytical Methods.

Polyamines and their derivatives were determined with the aid of high-performance liquid chromatography as described by Hyvönen et al. (Hyvönen, T., Keinänen, T. A., Khomutov, A. R., Khomutov, R. M., and Eloranta, T. O. (1992) J. Chromatogr. 574, 17–21). SSAT activity was assayed according to Bernacki et al. (Bernacki, R. J., Bergeron, R. J., and Porter, C. W. (1992) Cancer Res. 52, 2424–2430). α-Amylase activity was determined from heparinized plasma using an analyzer system Microlab 200 from E. Merck (Darmstadt, Germany). The Activity of ODC was assayed essentially as described in (Jänne, J. and Williams-Ashman, H. G. (1971 J. Biol. Chem. 246, 1725–1732). The polyamine oxidase (PAO) activity was assayed essentially as described by (Kumazawa, T., Seno, H., and Suzuki, O. (1990), Anal Biochem 188,105–108) using $N^1$, $N^{11}$-diacetylnorspermine, instead of $N^1$-acetylspermine as substrate.

Histological Analyses of the Pancreatic Specimens.

Formalin-fixed pancreatic specimens were embedded in paraffin, cut into 5-μm-thick slices, and stained with hematoxylin/eosin. The stained sections were coded and scored by the participating gastroenterologist (K.-H. H.) according to the method of Niederau et al. (Niederau, C., Liddle, R. A., Ferrell, L. D., and Grendell, J. H. (1986) J. Clin. Invest. 78, 1056–1063). The details of the histological scoring are presented in Table A and Tables 4 A/B/C.

Immunohistochemistry of Proliferating Cell Nuclear Antigen (PCNA).

PCNA was detected from formalin-fixed paraffin-embedded tissue section as described in detail earlier (Alhonen, L., Räsänen, T. L., Sinervirta, R., Parkkinen, J. J., Korhonen, V. P., Pietilä, M., and Jänne, J. (2002) Biochem. J. 362, 149–15).

Statistical Analyses.

The data are expressed as means ±SD. One-way analysis of variance (ANOVA) with Dunnett's post hoc test for multiple comparisons was used for statistical analyses with the aid of a software package, GraphPad Prism 3.0 (GraphPad Software, Inc., San Diego, Calif.).

Example 1

Depletion of Pancreatic Polyamines by Zinc.

Administration of zinc (10 mg/kg) alone or with methylspermidine (50 mg/kg) did not influence SSAT activity in syngenic rats while in transgenic rats the enzyme activity rose from 36±7.1 to 4270±560 pmol/mg/10 min in response to zinc. Inclusion of the analogue with zinc only slightly increased SSAT activity over that achieved with zinc alone. The changes in pancreatic polyamine pools in response to zinc and methylspermidine are depicted in FIG. 1. Putrescine pools (FIG. 1a) remained very low regardless of the treatment in non-transgenic animals whereas transgenic animals typically showed very high putrescine pool already without any treatments indicative of constitutive activation of polyamine catabolism. The various treatments only marginally altered pancreatic putrescine pools (FIG. 1a). Pancreatic spermidine pool remained virtually unaltered after zinc alone or in combination with the analogue in the syngenic animals (FIG. 1b), but was dramatically (by 90%) reduced in transgenic animals in response to zinc. Administration of methylspermidine had little effect on zinc-induced depletion of spermidine (FIG. 1b). While zinc alone or in combination appeared to decrease pancreatic spermine pool in syngenic animals, its effect in transgenic animals was much more striking, as spermine pool was decreased by more than 80% (FIG. 1c). FIG. 1d depicts the accumulation of the analogue in the pancreas after a single dose or two doses. As indicated in the figure, the analogue effectively accumulated in the pancreas apparently with no further metabolism.

Example 2

Effect of Methylspermidine on Zinc-induced Pancreatitis.

Figure 2:
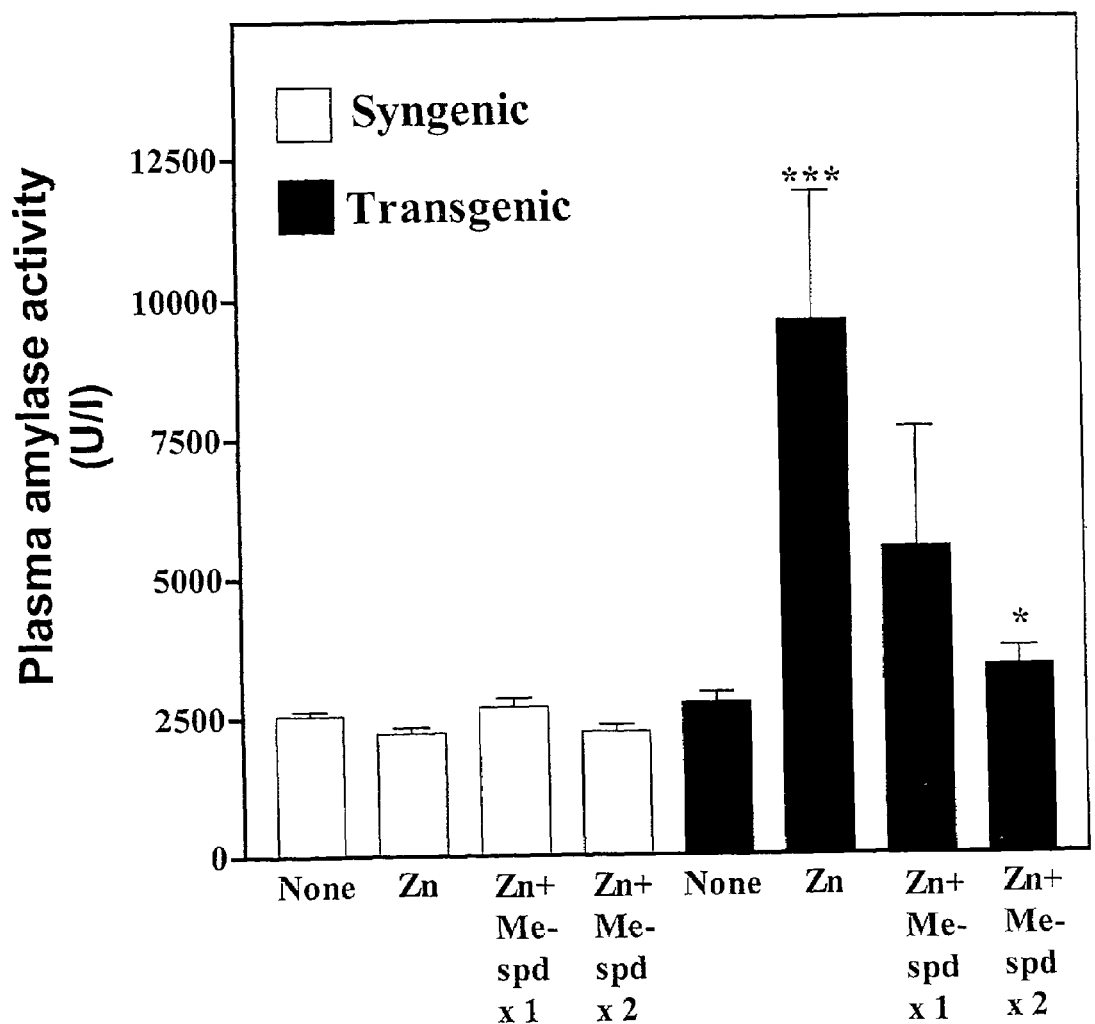
FIG. 2. Plasma α-amylase activity in syngenic and transgenic rats after zinc and methylspermidine. The animals were treated as in FIG. 1. Six to eight animals in each group. *p<0.05 as compared with zinc-treated animals. ***p<0.001 as compared with untreated animals. Me-spd, methylspermidine.
Figure 3:
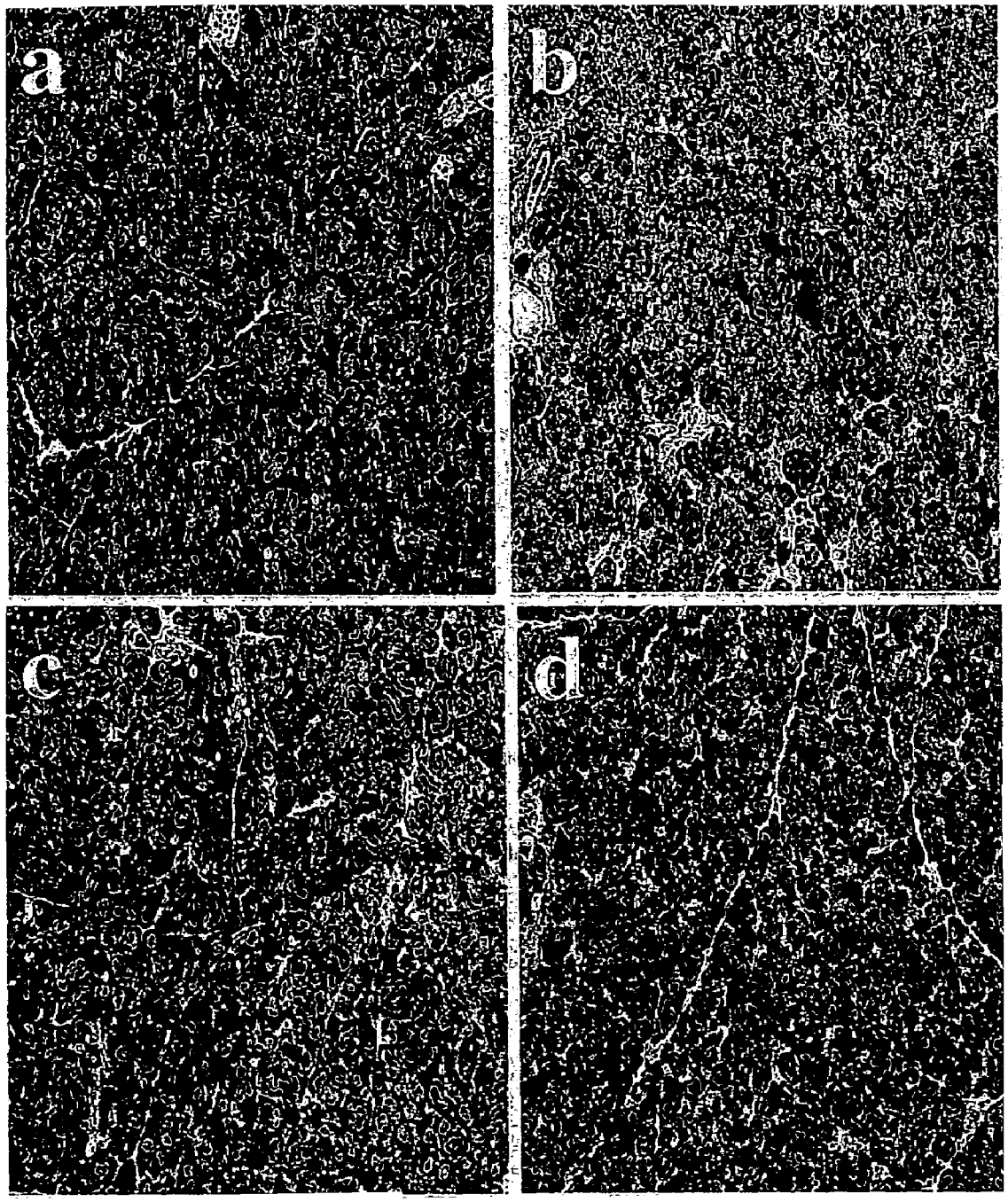
FIGS. 3a–3d. Histology of pancreas of transgenic rats after zinc and methylspermidine. The animals were treated as in FIGS. 1a–1d. Magnification ×125.

FIG. 2. shows plasma α-amylase activity after a single dose of zinc alone or in combination with analogue. Amylase activity remained at low level in syngenic animals regardless of the treatments, was significantly increased after zinc in transgenic rats indicating the development of pancreatitis, but was decreased after a single dose and fully normalized after two repeated doses of methylspermidine. FIG. 3 depicts pancreatic histology in transgenic animals after saline (FIG. 3a), after zinc alone (FIG. 3b), after zinc and single dose of the analogue (FIG. 3c) and after zinc and two doses of the analogue (FIG. 3d). The acinar structure of untreated transgenic animal is entirely normal (FIG. 3a) whereas zinc induced distinct pancreatitis with more than 50% of the acinar cells undergoing necrosis (FIG. 3b). Administration of methylspermidine prior to zinc injection dramatically improves the situation, as very little necrosis was present after a single dose of the analogue (FIG. 3c) and none after two doses of the analogue (FIG. 3d). Table A summarizes the histological scoring of pancreatic specimens from all animals. As indicated in the table, pancreatic histology was only marginally affected by the treatments in syngenic animals while transgenic animals showed acute pancreatitis after zinc with acinar necrosis as a prominent feature. A single dose of the analogue administered prior to zinc reduced the extent of necrosis while after two repeated doses of the compound very little, if any, necrosis was present (Table A).

TABLE A

| Animals and treatments | Scoring of histological alterations | | | |
|---|---|---|---|---|
| | Histological scoring (0 to 4) | | | |
| | Edema | Vacuolization | Inflammation | Necrosis |
| Sg + none (n = 6) | 0 | 0 | 0 | 0 |
| Sg + Zn (n = 7) | 1 | 0 | 1–2 | 0 |
| Sg + Zn + 1 × Me-spd (n = 6) | 1 | 0 | 1 | 0 |
| Sg + Zn + 2 × Me-spd (n = 8) | 1 | 0 | 0 | 0 |
| Tg + none (n = 6) | 0 | 0 | 0 | 0 |
| Tg + Zn (n = 7) | 1–2 | 1–2 | 1 | 3–4 |
| Tg + Zn + 1 × Me-spd (n = 7) | 1 | 0 | 1 | 2 |
| Tg + Zn + 2 × Me-spd (n = 8) | 1 | 1 | 1 | 0–1 |

The histological changes were scored blindly by a gastroenterologist (K.-H. H). The scores range from 0 (absent), 1 (minimal) to 4 (maximal). The scores for necrosis and vacuolization refer to an approximate percentage of cells involved.
0, 0–5%;
1, 5–15%;
2, 15–35%;
3, 35–50%;
4, >50%.
Sg, syngenic;
Tg, transgenic;
Me-spd, methylspermidine.

Treatment of rats with Me$_2$Spm (25 mg/kg 2 injections i.p. 20/4 hours prior to zinc) also prevents pancreatitis in rats with depleted polyamine pools, as shown in Example 13, infra.

Example 3

Effect of Partial Hepatectomy on Hepatic Polyamine Pools in Syngenic and Transgenic Rats.

Figure 4:
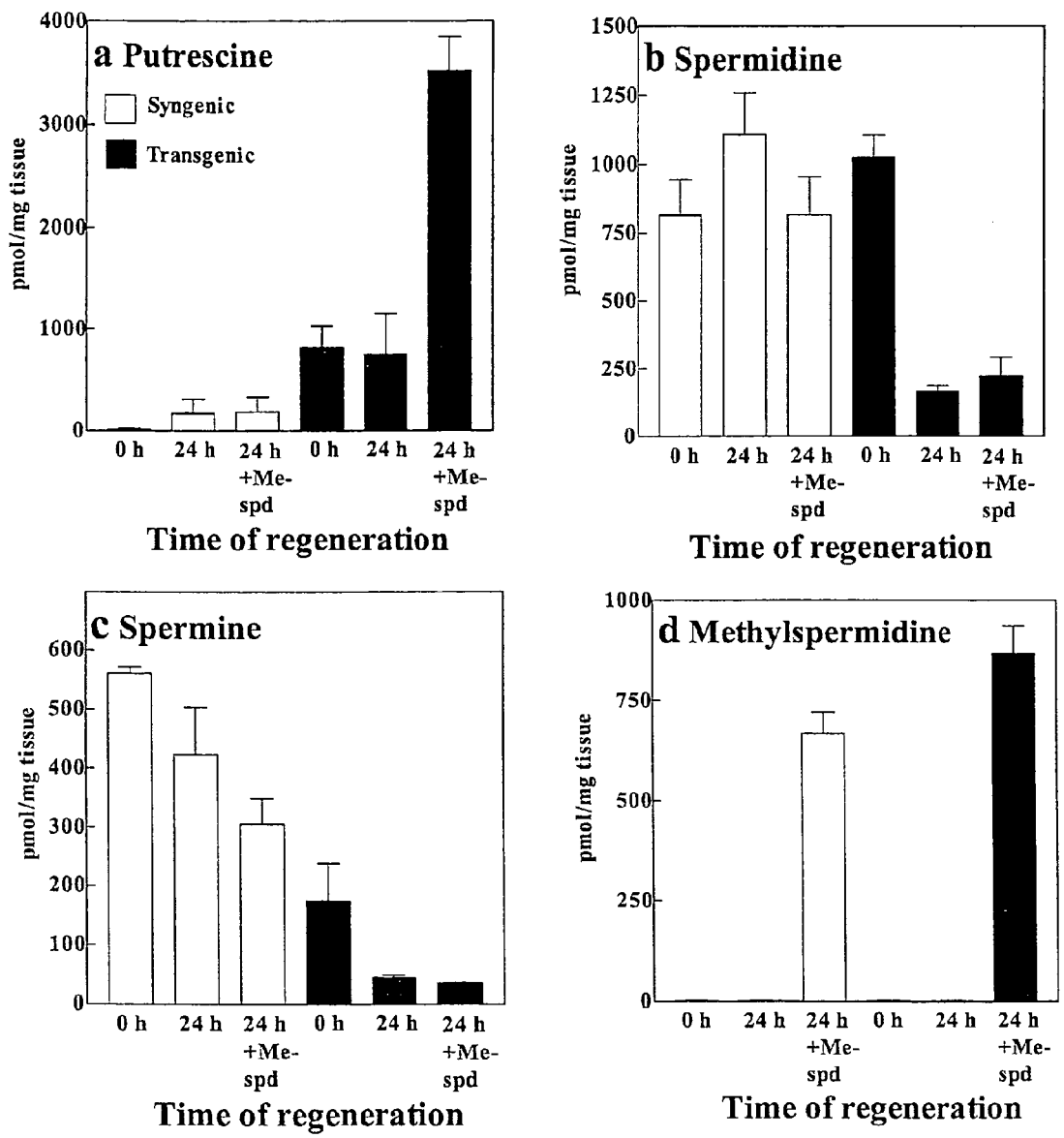
FIGS. 4a–4d. Hepatic polyamine pools in syngenic and transgenic rats after partial hepatectomy and methylspermidine. Methylspermadine (50 mg/kg) was given as a single dose 3 h before partial hepatectomy. Three to five animals in each group. Me-spd, methylspermidine.

Partial hepatectomy did not affect the low hepatic SSAT activity in non-transgenic rats while the enzyme activity rose from preoperative level of 12.7±6.0 to 4500±1040 pmol/mg/10 min at 24 h postoperatively. A single dose of methylspermidine given 3 h prior to the operation further enhanced SSAT activity to 7520±3000 pmol/mg/10 min at 24 h postoperatively. FIG. 4 depicts polyamine concentrations in syngenic and transgenic rats at 24 h after partial hepatectomy. Putrescine pool (FIG. 4a) distinctly increased in syngenic animals in response to the operation. Transgenic animals showed high putrescine concentration already before operation that was not affected by the operation, but was strikingly increased in response to the analogue. This in all likelihood reflected the enhanced SSAT activity. Spermidine pool (FIG. 4b) was typically expanded in response to the operation in syngenic animals, whereas the transgenic animals showed a dramatic reduction of spermidine level at 24 h postoperatively (FIG. 4b). Hepatic spermine pool (FIG. 4c) was also typically decreased in syngenic animals after partial hepatectomy. In transgenic animals, the low spermidine pool was further decreased in response to the operation (FIG. 4c). Methylspermidine had little effect on hepatic spermidine and spermine concentrations. FIG. 4d indicates that the analogue was effectively accumulated in normal and transgenic liver.

Example 4

Effect of Partial Hepatectomy and Methylspermidine on Liver Weight Gain and Proliferative Activity.

Figure 5:
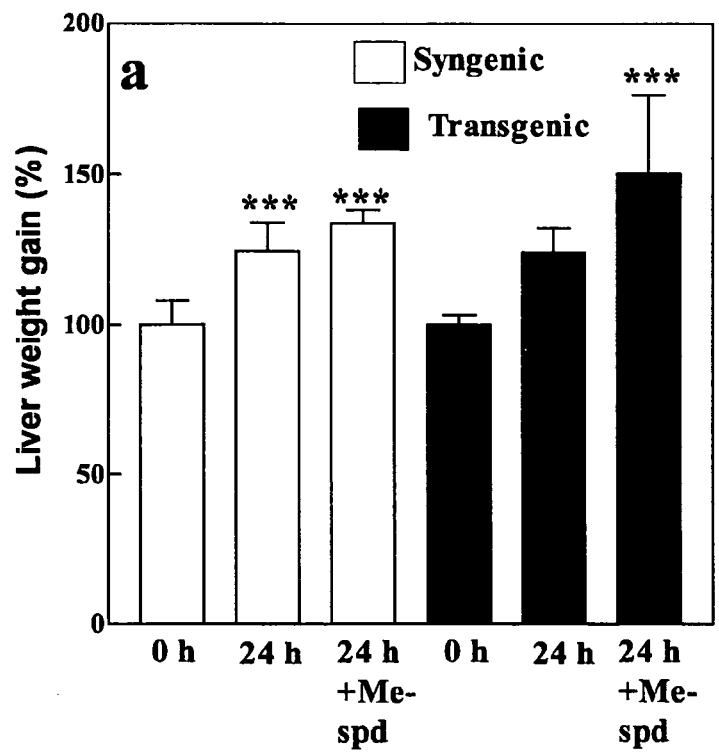
FIGS. 5a–5b. Liver weight (FIG. 5a) and PCNA labeling index (FIG. 5b) in syngenic and transgenic rats after partial hepatectomy and methylspermidine. Three to five animals in each group. *$p<0.05$, ***$p<0.001$ as compared with preoperative values. Md-spd, methylspermidine.
Figure 5:
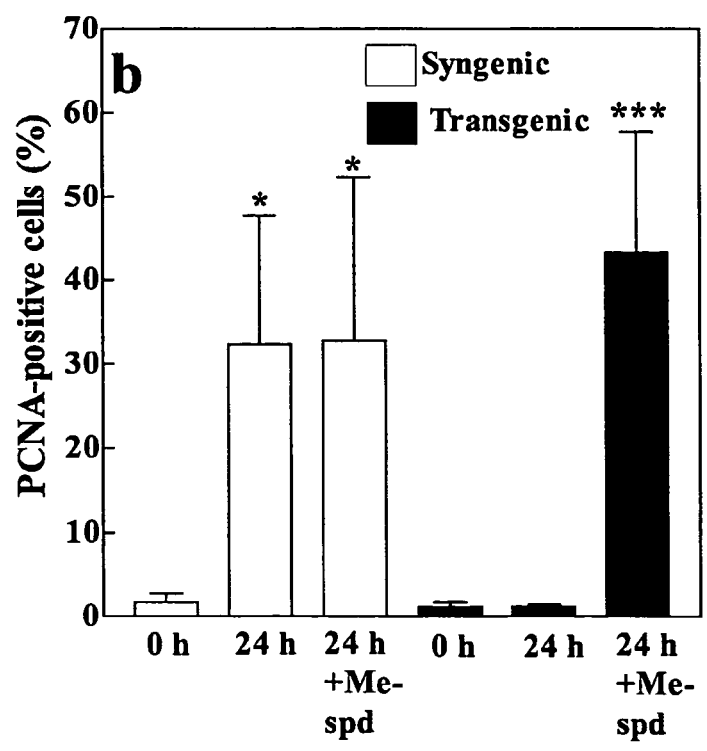

FIG. 5 shows liver weight gain (a) and proliferative cell nuclear antigen (PCNA) labeling index (b) at 24 h after partial hepatectomy without or with a prior injection of methylspermidine in syngenic and transgenic animals. The weight of the liver remnant was significantly increased in syngenic, but not transgenic animals, at 24 h after the operation (FIG. 5a). Methylspermidine had no effect on the weight gain in non-transgenic animals, but significantly increased the organ weight in transgenic animals (FIG. 5a). PCNA was used as an indicator of proliferative activity during liver regeneration. Immunohistochemical detection of PCNA is a convenient and commonly used method to grade proliferative activity in various tissues. PCNA expression is closely correlated with the S-phase of the cell cycle (17). FIG. 5b depicts PCNA labeling index before partial hepatectomy and at 24 h postoperatively in syngenic and transgenic rats without or with methylspermidine treatment. In resting liver, only about 1% of the hepatocytes were PCNA-positive. In syngenic animals, the number of PCNA-positive cells increased sharply to over 30% at 24 h after the operation whereas in transgenic animals the number of positive cells remained at the low preoperative level at this time point (FIG. 5b). Administration of the analogue did not change PCNA labeling index in syngenic livers, but dramatically increased the number of PCNA-positive cell in transgenic liver from about 1% to more than 40% (FIG. 5b). The experiment was repeated with other groups of syngenic and transgenic rats. In this experiment, PCNA-positive hepatocytes accounted for 0.5±0.1% in resting syngenic liver. The number of positive cells rose to 10.7±3.5% at 24 h postoperatively without the analogue (p<0.001) and to 9.8±1.5% with the analogue (p<0.001). The corresponding figures for the transgenic animals were 0.20±0.0 before the operation, 0.42±0.24% at 24 h postoperatively without methylspermidine and 25.9±4.9% with methylspermidine (p<0.001). It thus appears that the analogue completely reversed the proliferative block in transgenic livers.

Using transgenic rats with activated polyamine catabolism, zinc-induced pancreatitis is prevented by a prior administration of 1-methylspermidine, a metabolically stable analogue of spermidine that is thought to fulfill most of the putative cellular functions of spermidine. In a similar fashion, the analogue alleviates in transgenic rats the proliferative block, which in all likelihood is caused by spermidine depletion during early liver regeneration. Thus, it appears that spermidine is specifically involved in the maintenance of pancreatic integrity and in the initiation of liver regeneration. Administration of a metabolically stable analogue of spermidine such as, for example, 1-methylspermidine may be used for the treatment and/or prevention of pancreatitis as well as the induction of liver regeneration.

For additional discussion, see Räsänen T L, Alhonen L, Sinervirta R, Keinänen T, Herzig K H, Suppola S, Khomutov A R, Vepsäläinen J, Jänne J., A polyamine analogue prevents acute pancreatitis and restores early liver regeneration in transgenic rats with activated polyamine catabolism, *J. Biol. Chem.* (2002) Oct 18;277(42):39867–72, the disclosure of which is hereby incorporated herein by reference in its entirety.

In addition, administration of metabolically stable analogues of spermidine such as, for example, 1-methylspermidine may be used to treat and/or prevent pancreatitis arising from causes other than those described above.

Example 5

Effect of Methylspermidine on Arginine-induced Pancreatitis.

Figure 6:
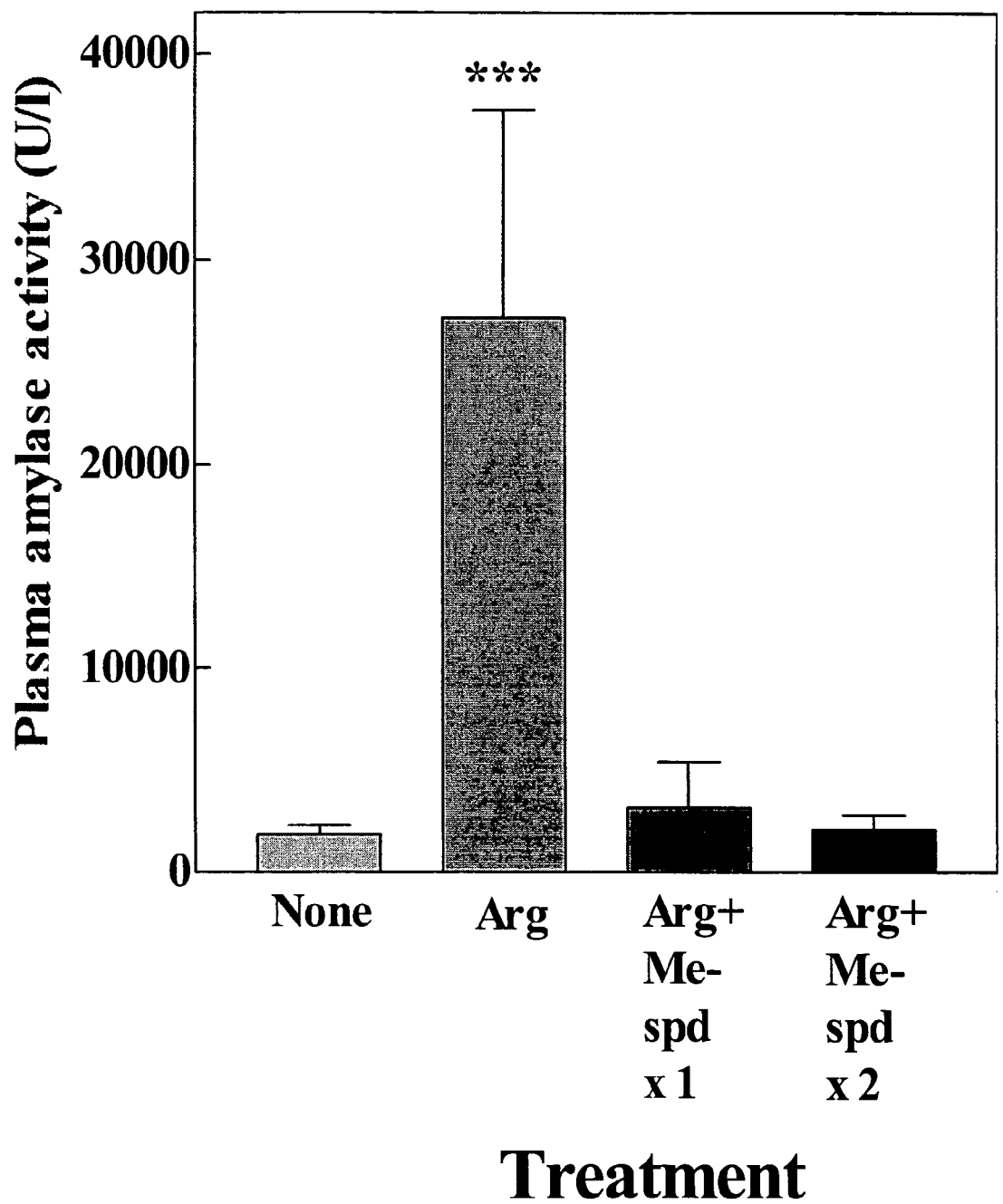
FIG. 6 Plasma α-amylase activity in rats with arginine-induced pancreatitis after methylspermidine. The animals received arginine (250–500 mg/kg) 24 h before sacrifice with or without methylspermidine (50 mg/kg) either as a single dose 4 h before arginine or as two doses 20 h and 4 h before arginine. Three to five animals in each group. Arg, Arginine. Me-Spd, methylspermidine.

Administration of large quantities of arginine is known to cause acute, necrotizing pancreatitis in rats. Preliminary results demonstrate that arginine activates polyamine catabolism in pancreas. FIG. 6 shows plasma α-amylase activity in rats after administration of (250–500 mg/kg) arginine. Amylase activity was significantly increased in arginine-treated animals, indicating the development of pancreatitis. Administration of a single dose of methylspermidine (50 mg/kg) significantly reduced the pancreatitis-associated increase in plasma amylase. After two repeated doses of methylspermidine, plasma amylase levels were fully normalized. Methylspermidine administration also prevented the histopathological changes in the pancreas associated with arginine-induced pancreatitis.

Example 6

Effect of Methylspermidine on Cerulein-induced Pancreatitis.

Figure 7:
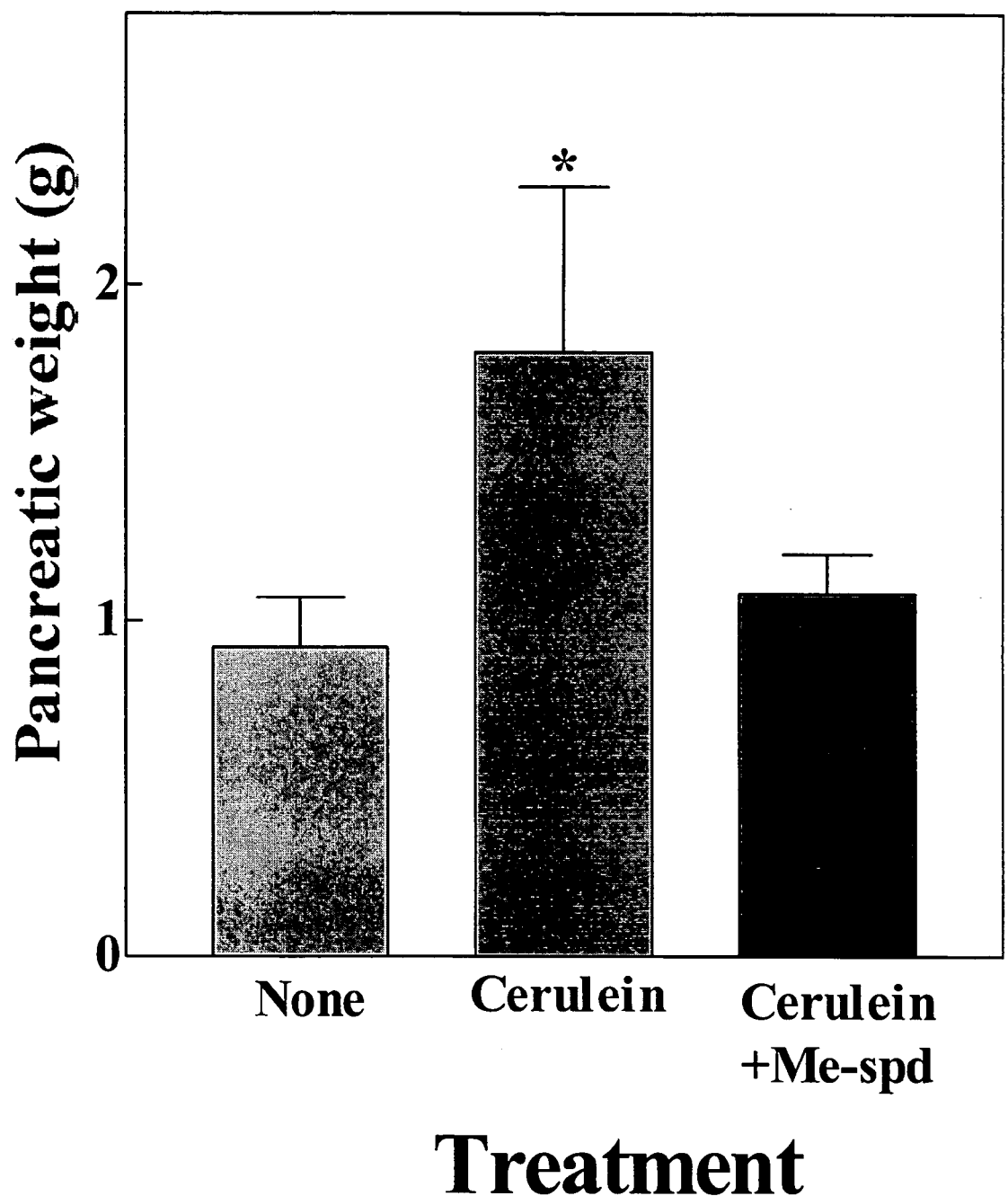
FIG. 7 Effect of pancreatic-associated edema by methylspermidine in rats with cerulein-induced pancreatitis. The animals received cerulein 24 h before sacrifice with or without methylspermidine (50 mg/kg) as a single dose 4 h before cerulein. Three to five animals in each group. Me-Spd, methylspermidine.

Administration of cerulein induces a non-necrotizing pancreatitis in rodents. Cerulein-induced pancreatitis is characterized by a pronounced increase in plasma/serum amylase activity. Administration of methylspermidine does not normalize amylase levels in this animal model. FIG. 7 shows that a single dose (50 mg/kg) of methylspermidine reduces the pancreatitis-associated edema of animals with cerulein-induced pancreatitis.

Example 7

Stability of the Analogues in the Liver of SSAT Transgenic Rats.

Figure 8:
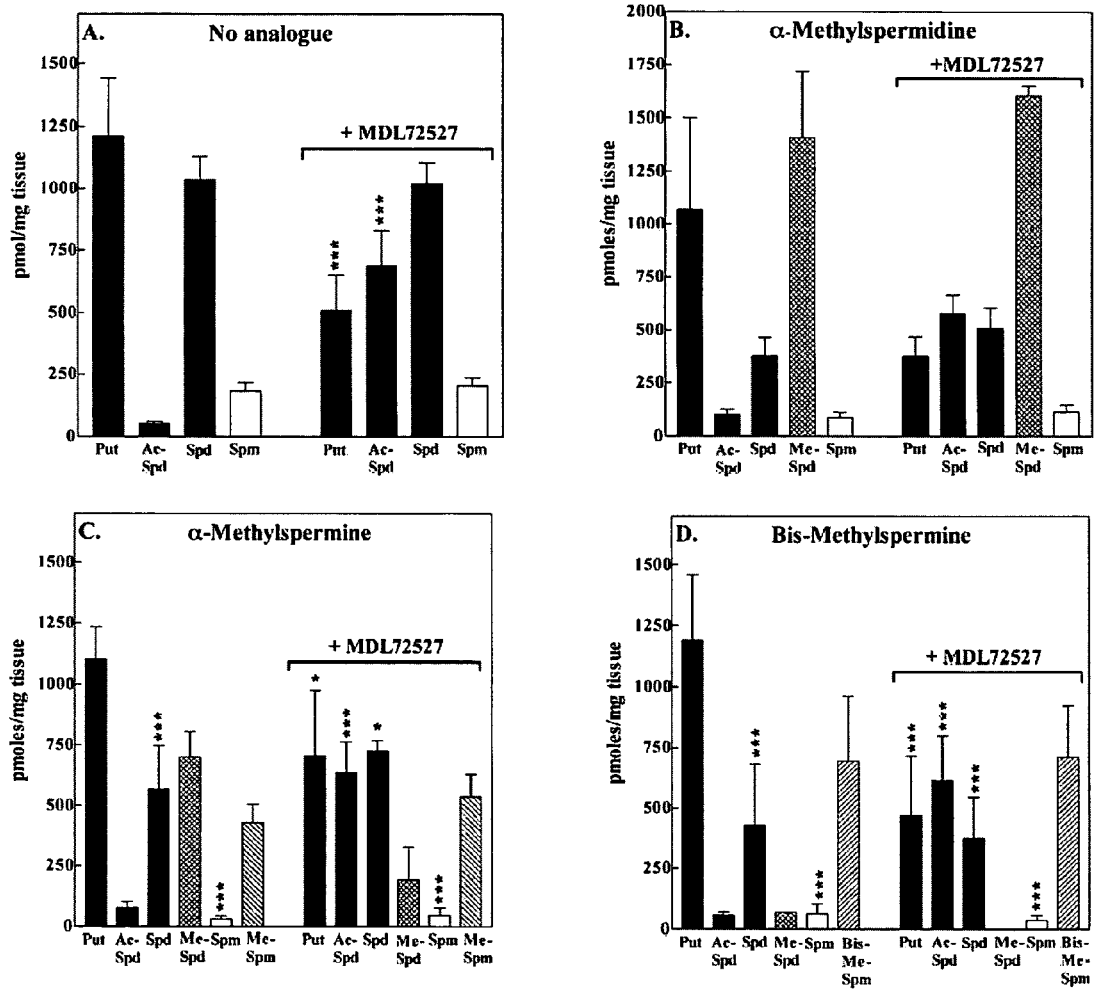
FIGS. 8A–8D. Hepatic polyamine pools in SSAT transgenic rats treated with methylated polyamine analogues without or with MDL72527. The rats were injected twice with MDL72527 (50 mg/kg i.p.) at 16-h interval. The polyamine analogues (25 mg/kg i.p.) were injected 2 and 8 h later. The animals were sacrificed 24 h after the last MDL72527 injection. There were three to four animals in each group. Put, putrescine; Ac-Spd, $N^1$-acetylspermidine; Spd, spermidine; Me-Spd, α-methylspermidine; Me-Spm, α-methylspermine; Bis-Me-Spm, bis-α-methylspermine. *$p<0.05$, ***$p<0.001$ as compared with untreated animals.

FIG. 8A displays the typical polyamine pattern in the liver of SSAT overexpressing rats. Putrescine pool was greatly expanded while spermine level was decreased. An exposure of the rats to the polyamine oxidase (and spermine oxidase) inhibitor MDL72527 expectedly greatly reduced putrescine content and increased the pool of $N^1$-acetylspermidine (FIG. 8A). All the analogues accumulated in the liver of the transgenic rats, α-methylspermidine showing the highest tissue concentrations (FIG. 8A–D). The latter analogue likewise appeared to be metabolically stable and, in contrast to an earlier report (Lakanen, J. R., Coward, J. K. and Pegg, A. E. (1992) J. Med. Chem. 35, 724–734), the inventors found no evidence that α-methylspermidine would have been converted to α-methylspermine (FIG. 8B). As indicated in FIG. 8C, α-methylspermine was effectively converted to α-methylspermidine. The latter conversion was markedly inhibited by the MDL72527 compound (FIG. 8C). FIG. 8D shows that also bis-α-methylspermine was converted to α-methylspermidine, but less effectively than α-methylspermine. The conversion of bis-α-methylspermine to α-methylspermidine was totally prevented by MDL72527 (FIG. 8D).

Example 8

Effect of the α-methylated Analogues on SSAT and PAO Activities.

Figure 9:
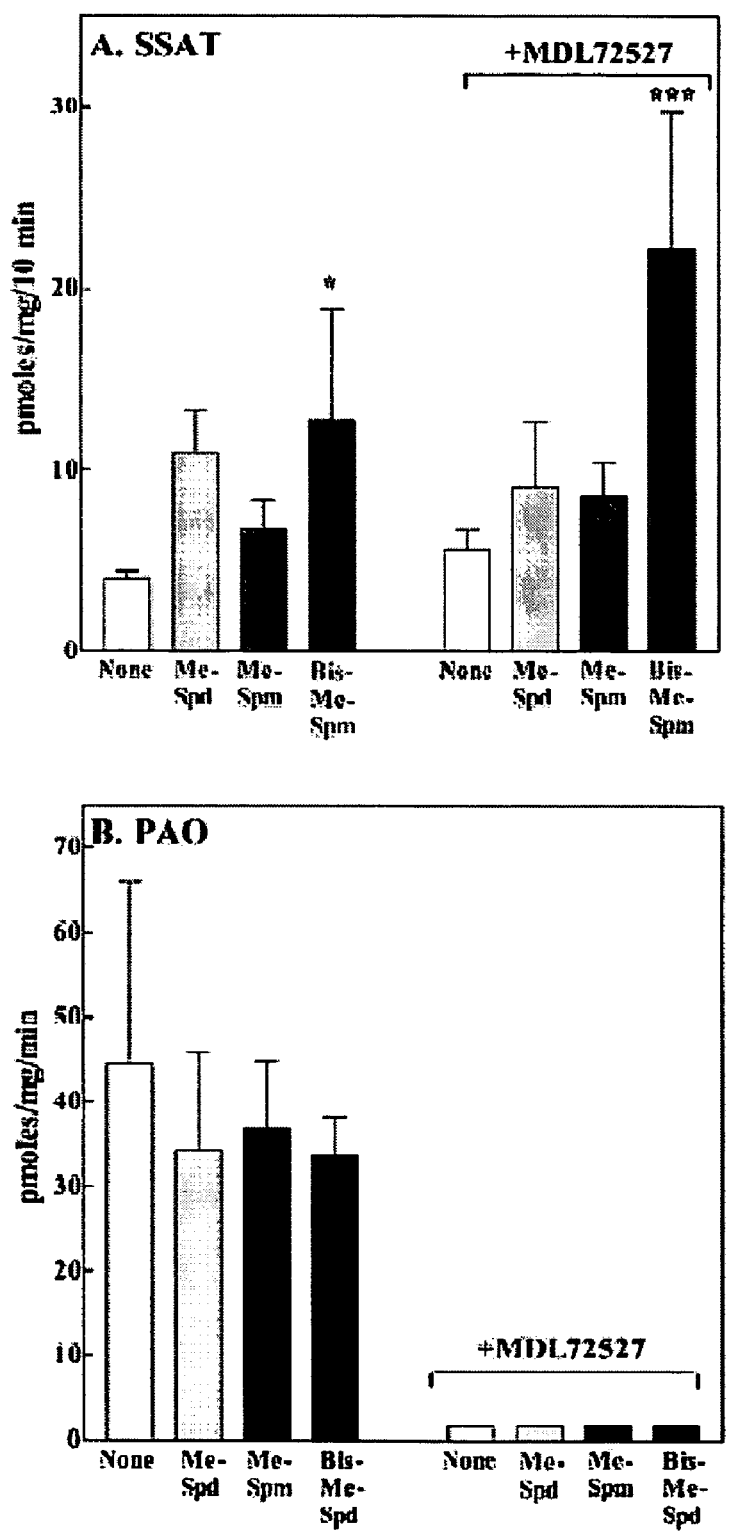
FIGS. 9A–9B. Effect of polyamine analogues without or with MDL72527 on hepatic SSAT (FIG. 9A) and PAO (FIG. 9B) activities in SSAT transgenic rats. The rats were treated with the drugs as described in the legend for FIGS. 8A–8D. There were three to four animals in each group. Me-Spd, α-methylspermidine; Me-Spm, α-methylspermine; Bis-Me-Spin, bis-α-methylspermine. *$p<0.05$, ***$p<0.001$ as compared with untreated animals.

PAO activity was measured to verify the effectiveness of MDL72527 treatment and to determine whether the analogues have any effect on its activity. Polyamines and especially their N-alkylated derivatives have been previously shown to induce SSAT activity. In the present study, the α-methylated polyamine analogues did not appear to be very effective inducers of SSAT activity. In fact, only bis-α-methylspermine significantly increased hepatic SSAT activity, which was further enhanced by combining the latter analogue with MDL72527 (FIG. 9A). However, the modest induction of the SSAT activity in response to the α-methylated analogues may be tissue-specific as the analogues much more effectively induced SSAT activity in pancreas of the transgenic rats. The analogues had little effect on PAO activity while the used doses of MDL72527 alone or in combination with the analogues virtually completely inhibited PAO activity (FIG. 9B). All the analogues stimulated ODC activity to some extent. In the case of MeSpm, SSAT induction may increase the metabolism of parent compound to MeSpd.

Example 9

Studies with Liver Extracts Obtained from Wild-type Rats.

In vitro trials were used to investigate the stability of methylated polyamine analogues. High-salt liver extracts were used to remove or decrease the content of small-molecular weight compounds. As the extraction procedure certainly removed any acetyl-CoA (and probably also inactivated the labile SSAT protein), the inventors used benzaldehyde that is known to greatly enhance PAO activity when spermidine or spermine is used as the substrate (but possibly not when $N^1$-acetylspermidine is used) (Höltta, E. (1977) *Biochemistry* 16, 91–100). Benzaldehyde in all likelihood forms a Schiff base with the polyamines mimicking the structure and charge distribution of acetylated polyamines which are much more preferred substrates for PAO than the unmodified polyamines (Hölttä, E. (1977) *Biochemistry* 16, 91–100). As shown in Table 1, substantial amounts of spermidine and spermine (but no putrescine) remained in the extracts even after the high-salt procedure. During incubation for 60 min, some putrescine was formed that was greatly enhanced upon an inclusion of 5 mM benzaldehyde in the incubation mixture. Interestingly, the formation of putrescine was associated with the disappearance of the endogenous spermine, but not spermidine. However, the view that spermine was directly converted to putrescine was ruled out by tracer studies indicating that labeled spermine was first converted to spermidine followed by the appearance of the label in putrescine (results not shown). Putrescine formation was sensitive to MDL72527 in the absence and presence of benzaldehyde. Inclusion of 1 mM $N^1$-acetylspermidine yielded large amounts of putrescine the formation of which was not enhanced by benzaldehyde. In fact, the observed slight inhibition in the presence could be attributable to the formation of $N^8$ Schiff base. Again, MDL72527 prevented any formation of putrescine from $N^1$-acetylspermidine (Table 1). In comparison with $N^1$-acetylspermidine, 1 mM spermidine produced relatively little putrescine even in the presence of benzaldehyde. Inclusion of 1 mM α-methylspermidine appeared to yield some putrescine in the presence of benzaldehyde, but this putrescine was in all likelihood derived from endogenous spermine (Table 1). Exogenous spermine was converted to spermidine even in the absence of benzaldehyde. The conversion was greatly enhanced by the latter compound. Inclusion of 1 mM α-methylspermine yielded substantial amounts of spermidine and α-methylspermidine already without benzaldehyde, which further enhanced the conversions by a factor of about 3 (Table 1). The only product derived from 1 mM bis-α-methylspermine was α-methylspermidine, the formation of which was stimulated nearly 5-fold by benzaldehyde. It is interesting to note that bis-α-methylspermine was even more effectively converted to α-methylspermidine in the presence of benzaldehyde than was α-methylspermine. The metabolism of spermine and its α-methylated derivatives was fully or partially blocked by MDL72527 (Table 1).

TABLE 1

Metabolism of polyamines and their analogues in rat liver extracts

| Treatment | Polyamine or analog (pmoles/mg prot) | | | |
| --- | --- | --- | --- | --- |
| | Putrescine | Spermidine | αMeSpd | Spermine |
| liver extracts | | | | |
| without 1 h + 37° C. incubation | nd | 796 ± 27 | | 1486 ± 191 |
| after 1 h + 37° C. incubation | 70 ± 45 | 824 ± 68 | | 1270 ± 88 |
| +5 mM benzaldehyde | 635 ± 22 | 825 ± 110 | | 20 ± 34 |
| +250 μM MDL72527 | 51 ± 24 | 739 ± 116 | | 1427 ± 119 |
| +5 mM BA and 250 μM MDL72527 | 4 ± 5 | 835 ± 49 | | 1265 ± 111 |
| 1 mM $N^1$-acetylspermidine[a] | 18882 ± 936 | 1120 ± 103 | | 1515 ± 314 |
| +5 mM benzaldehyde | 15075 ± 1125 | 1079 ± 213 | | 1185 ± 67 |
| +250 μM MDL72527 | nd | 1211 ± 141 | | 1299 ± 74 |
| +5 mM BA and 250 μM MDL72527 | nd | 899 ± 145 | | 1601 ± 93 |
| 1 mM Spermidine[a] | 186 ± 24 | [a] | | 905 ± 78 |
| +5 mM benzaldehyde | 3327 ± 287 | [a] | | 310 ± 83 |
| +250 μM MDL72527 | 44 ± 30 | [a] | | 876 ± 78 |
| +5 mM BA and 250 μM MDL72527 | 9 ± 10 | [a] | | 784 ± 51 |
| 1 mM α-methylspermidine[a] | nd | 394 ± 10 | [a] | 839 ± 130 |
| +5 mM benzaldehyde | 1030 ± 55 | 620 ± 74 | [a] | 210 ± 72 |
| +250 μM MDL72527 | nd | 387 ± 9 | [a] | 733 ± 54 |
| +5 mM BA and 250 μM MDL72527 | nd | 344 ± 12 | [a] | 789 ± 123 |
| 1 mM Spermine[a] | nd | 3140 ± 391 | | [a] |
| +5 mM benzaldehyde | nd | 21018 ± 1698 | | [a] |
| +250 μM MDL72527 | nd | 397 ± 64 | | [a] |
| +5 mM BA and 250 μM MDL72527 | nd | 659 ± 39 | | [a] |
| 1 mM α-methylspermine[a] | nd | 1827 ± 172 | 3097 ± 391 | 441 ± 36 |
| +5 mM benzaldehyde | nd | 6244 ± 107 | 9223 ± 265 | 343 ± 25 |
| +250 μM MDL72527 | nd | 735 ± 99 | nd | 375 ± 18 |
| +5 mM BA and 250 μM MDL72527 | nd | 568 ± 141 | nd | 389 ± 33 |
| 1 mM Bis-α-methylspermine[a] | nd | 744 ± 89 | 4389 ± 681 | 1109 ± 140 |
| +5 mM benzaldehyde | nd | 999 ± 66 | 20405 ± 1284 | 640 ± 85 |
| +250 μM MDL72527 | nd | 697 ± 81 | 617 ± 32 | 968 ± 123 |
| +5 mM BA and 250 μM MDL72527 | nd | 746 ± 42 | 602 ± 26 | 1054 ± 61 |

The liver extracts were prepared as described under "Materials and Methods" and incubated for 60 min at 37° C. with the indicated additions. MDL72527 containing reactions were preincubated for 10 min with the drug before polyamine/analogue addition. The concentration of added polyamine/analogue was 1 mM, benzaldehyde was 5 mM and MDL72527 (MDL) 250 μM.
n.d., not detected;
[a] in the beginning of the reaction polyamine/analogue equaled 84 700 pmoles/mg protein.
Me-Spd, α-methylspermidine.

Example 10

Substrate Specificity of the Purified Recombinant Spermine Oxidase (SMO) and Polyamine Oxidase (PAO).

Spermine and its methylated derivatives were degraded both by PAO and SMO (TABLE 2). However, the reaction velocity of PAO is very slow without benzaldehyde treatment, thus clearly suggesting that $N^1$-acetylation is a rate limiting step of PAO mediated degradation of spermine. It appears that alpha methylation prevents acetylation by SSAT, thus increasing the stability of the compound toward PAO. Alpha methylation of spermine seemed to decrease reaction velocity of SMO to further increasing the potential biological half-life of the drug.

TABLE 2

Substrate specificity of the purified recombinant spermine oxidase (SMO) and polyamine oxidase (PAO).

| | | pmoles/μg/min | | |
|---|---|---|---|---|
| Enzyme | Substrate | Putrescine | Spermidine | α-Me-SPD |
| PAO | 1.0 mM $N^1$-Ac-SPD | 400 | N.D. | N.D. |
| SMO | 1.0 mM $N^1$-Ac-SPD | N.D. | N.D. | N.D. |
| PAO | 0.2 mM SPM | N.D. | 20 | N.D. |
| | 1.0 mM SPM | N.D. | 28 | N.D. |
| | 1.0 mM SPM + 5 mM BA | N.D. | 439 | N.D. |
| SMO | 0.2 mM SPM | N.D. | 518 | N.D. |
| | 1.0 mM SPM | N.D. | 503 | N.D. |
| | 1.0 mM SPM + 5 mM BA | N.D. | 330 | N.D. |
| PAO | 0.2 mM α-Me-SPM | N.D. | 11.2 | 13.7 |
| | 1.0 mM α-Me-SPM | N.D. | 12.7 | 15.3 |
| | 1.0 mM α-Me-SPM + 5 mM BA | N.D. | 78 | 302 |
| SMO | 0.2 mM α-Me-SPM | N.D. | 90 | 164 |
| | 1.0 mM α-Me-SPM | N.D. | 99 | 175 |
| | 1.0 mM α-Me-SPM +5 mM BA | N.D. | 93 | 149 |
| PAO | 0.2 mM bis-α-Me-SPM | N.D. | N.D. | 39 |
| | 1.0 mM bis-α-Me-SPM | N.D. | N.D. | 54 |
| | 1.0 mM bis-α-Me-SPM + 5 mM BA | N.D. | N.D. | 296 |
| SMO | 0.2 mM bis-α-Me-SPM | N.D. | N.D. | 103 |
| | 1.0 mM bis-α-Me-SPM | N.D. | N.D. | 116 |
| | 1.0 mM bis-α-Me-SPM + 5 mM BA | N.D. | N.D. | 120 |

Experiments were carried out in triplicates where 20 μl of the purified protein was used per total reaction volumne of 180 μl. Reaction buffer containing 0.1 M glycine-NaOH pH 9.5 and 5 mM DTT was used to study the metabolism of the p0olyamines and their α-methylated analogues in 0.2 or 1.0 mM concentrations. The reactions were initiated with the studied polyamine or analogues addition and the reaction tubes incubated at 37° C. water-bath for 60 min. Five millimolar freshly distilled benzaldehyde was used to decrease the $K_m$ value and to increase the reaction velocity of PAO according to (Hölttä, E. (1977) Biochemistry 16, 91–100). The reactions were stopped with the addition of 20 μl of 100 μM diaminohexane in 50% w/v sulphosalisylic acid and analyzed with HPLC as described for polyamine samples.

Example 11

Restoration of Early Liver Regeneration in Transgenic Rat Overexpressing SSAT by α-methylspermidine and bis-α-methylspermine.

Figure 10:
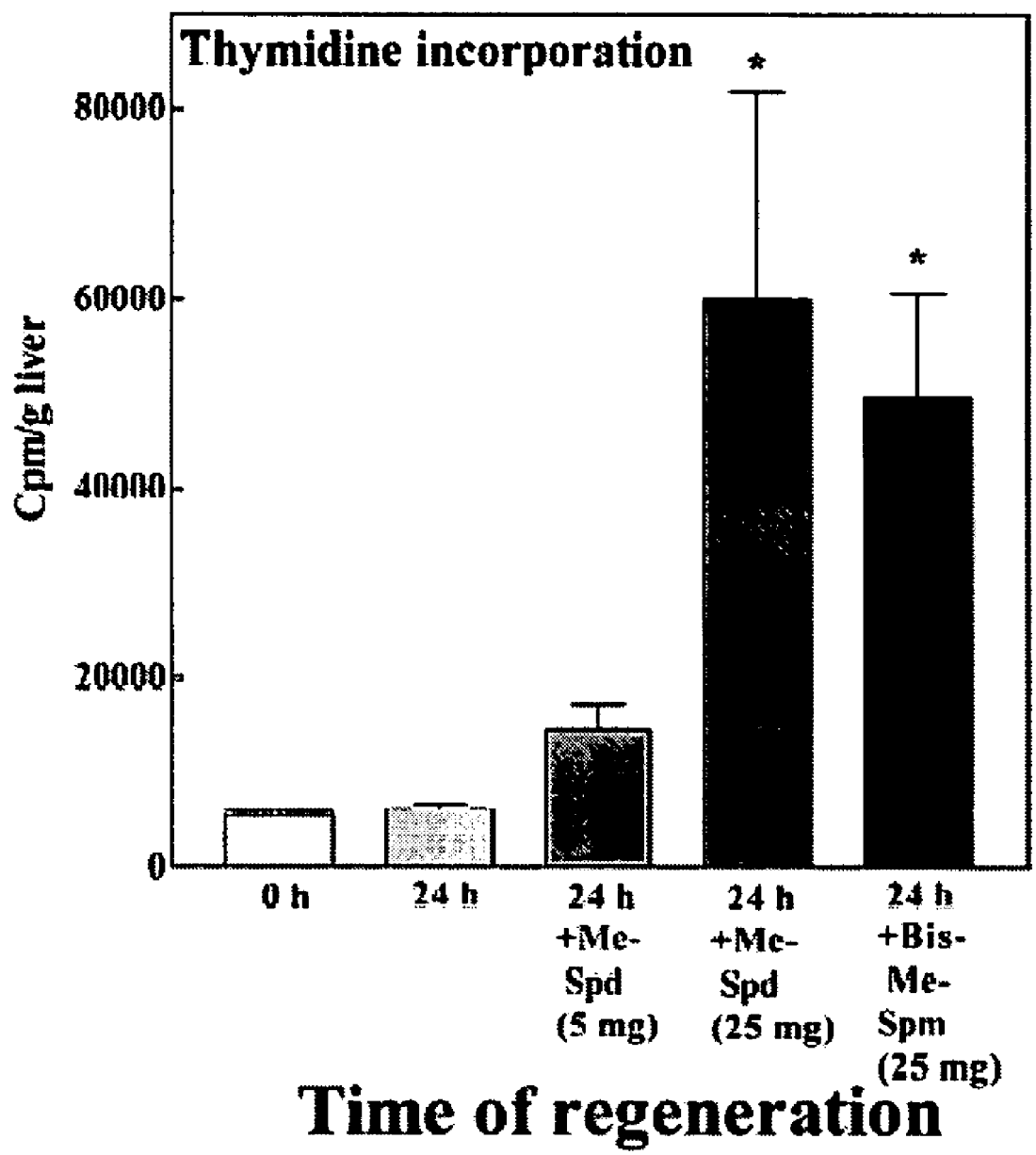
FIG. 10. Effect of polyamine analogues on thymidine incorporation in 24-h regenerating livers of SSAT transgenic rats. The animals were injected with 5 mg or 25 mg/kg of α-methylspermidine or 25 mg/kg of bis-α-methylspermine 20 h and 4 h before the operation. Ten μCi of tritiated thymidine was given 30 min before sacrifice. Three to four animals in each group. Me-Spd, α-methylspermidine; Bis-Me-Spm, bis-α-methylspermine. *$p<0.05$ as compared with unoperated animals.

The inventors had previously shown that partial hepatectomy of transgenic rats over expressing SSAT results in a profound spermidine and spermine depletion due to SSAT induction at 24 h postoperatively and failure to initiate liver regeneration (Räsänen, T. L., Alhonen, L., Sinervirta, R., Keinänen, T., Herzig, K. H., Suppola, S., Khomutov, A. R., Vepsäläinen, J., and Jänne, J. (2002) *J. Biol. Chem.* 277, 39867–39872, Alhonen, L., Räsänen, T. L., Sinervirta, R., Parkkinen, J. J., Korhonen, V. P., Pietilä, M., and Jänne, J. (2002) *Biochem. J.* 362, 149–153). Liver regeneration could be restored by a prior administration of α-methylspermidine (Räsänen, T. L., Alhonen, L., Sinervirta, R., Keinänen, T., Herzig, K. H., Suppola, S., Khomutov, A. R., Vepsäläinen, J., and Jänne, J. (2002) *J. Biol. Chem.* 277, 39867–39872). FIG. 10. depicts thymidine incorporation in livers of transgenic rats before and 24 h after partial hepatectomy. As shown, thymidine incorporation remained at the preoperative level at 24 h in untreated rats while small doses (5 mg/kg) of α-methylspermidine only insignificantly increased DNA synthesis. Higher doses (25 mg/kg) of both α-methylspermidine and bis-α-methylspermine resulted in about 10-fold stimulation of DNA synthesis (FIG. 10.). Table 3 lists the liver pools of polyamines and their analogues before and after partial hepatectomy. As found previously, partial hepatectomy brought about a profound depletion of spermidine and spermine at 24 h after the operation in these transgenic rats. The analogues were readily accumulated in the livers. Even though bis-α-methylspermine was converted to α-methylspermidine, the hepatic concentration of the latter compound remained clearly below (about one third) the level achieved with the smaller dose of α-methylspermidine that failed to stimulate thymidine incorporation (FIG. 10.). It thus appears that the observed stimulation of DNA synthesis after bis-α-methylspermine was attributable to the spermine derivative and not to α-methylspermidine. In fact, bis-α-methylspermine appeared to be even more effective for the induction of liver regeneration than α-methylspermidine on a molar basis.

TABLE 3

Accumulation of polyamines and their α-methylated analogues in regenerating liver.

| Time of regeneration/ Treatment | pmoles/mg tissue wet weight | | | | |
|---|---|---|---|---|---|
| | Put | Spd | Me-Spd | Spm | Me$_2$-Spm |
| 0 h | 1030 ± 95 | 1170 ± 140 | | 158 ± 45 | |
| 24 h | 4160 ± 1050[a] | 405 ± 91[a] | | 45 ± 31[a] | |
| 24 h + MeSpd (5 mg) | 4540 ± 690[a] | 183 ± 47[a] | 462 ± 41 | 18 ± 5[a] | |
| 24 h + MeSPD (25 mg) | 3570 ± 596[a] | 281 ± 107[a] | 864 ± 166 | 40 ± 24[a] | |
| 24 h + Me$_2$Spm (25 mg) | 4400 ± 275[a] | 266 ± 55[a] | 154 ± 6 | 6 ± 8[a] | 381 ± 124 |

Transgenic rats were partially hepatectomized and sacrificed at 24 h. The polyamine analogues were given 20 and 4 h before the operation (5 mg or 25 mg/kg). There were 3 to 4 animals in each group.
Put, putrescine;
Spd, spermidine;
MeSpd, α-methylspermidine;
Spm, spermine;
Me$_2$Spm, bis-α-methylspermine.
[a]$p < 0.001$ as compared to unoperated animals.

Example 12

The effect of α-methylspermidine to the Survival and Severity of Pancreatitis in SSAT Transgenic Rats.

Transgenic UKUR30 female rats (weighting about 200 g) were used for the experiments. Pancreatitis was initiated with zinc 10 mg/kg treatment. Experiments were separated in five different parts (Exp. 1–5). Animals treated with α-MeSPD received 50 mg/kg i.p at the indicated time point(s). The pooled data from all of the experiment is shown in tables 4 A/B/C/D. First histological signs of pancreatic failure were evident within 6 h after the zinc. Pancreatic failure steadily increases until 24 hours when the first animals died. Within 48 hours mortality was almost 70% in control zinc treated rats. Although, MeSpd treated animals showed severe signs pancreatic failure, only one animal died within 48 h, which was the end-point of all five experiments. Treatment beginning several hours after the induction of pancreatitis was effective, clearly indicating that MeSpd can be used in the treatment of acute pancreatitis in SSAT transgenic rats.

This model for acute pancreatitis is rapid and very progressive. The first histological signs of pancreatic inflammation are evident within six hours after zinc administration. Within 12 hours of zinc induction pancreatic failure is evident and the first animals to die did so before 24 hours. Within 48 hours mortality is as high as 70%. Amongst the MeSpd treated animals only one animal died, even though in some experiments treatment was started after 12 hours from induction of the disease. It appears from the detailed analysis that some animals did not respond to zinc injection. Overall, the results indicate that MeSpd is not only effective in the prevention (discussed supra) but also in the treatment of acute pancreatitis.

Natural Course of the Zinc Induced Acute Pancreatitis in SSAT Transgenic Rats and the Effect of MeSPD Treatment to the Survival of Animals.

Tables 4 A/B/C/D present the natural course of zinc induced pancreatitis. Histological scoring along with plasma amylase activity is shown as a measure of severity of pancreatitis. Tissue zinc and polyamine levels and SSAT activity were determined to verify the response of each animal to the treatment. No other data than the number of death animals is shown from deceased animals. Transgenic UKUR30 female rats weighting about 200 grams were used for the experiment. Zinc was injected i.p. 10 mg/kg to initiate acute pancreatitis. Animals treated with MeSpd received one 50 mg/kg dosage i.p. at the indicated time point(s). At indicated time points live animals were sacrificed and pancreas was subjected to further analysis. Histological scoring; edema and necrosis 0–4, PU, putrescine; SPD, spermidine; SPM, spermine; N$^1$AcSPD, N$^1$-acetylspermidine; MeSpd, α-methylspermidine. Values for polyamines are expressed as pmoles/mg/wet weight. SSAT pmoles/10 min/mg wet weight.

TABLE 4A

| Treatment | MeSpd treatment | Exp. | Edema | Necrosis | Zn (mg/dm$^3$) | P-amyl (U/l) | SSAT | PU | SPD | SPM | N$^1$AcSPD |
|---|---|---|---|---|---|---|---|---|---|---|---|
| none | none | 1 | 0 | 0 | 7.4 | 3376 | 28 | 4402 | 3480 | 554 | 60 |
| none | none | 1 | 0 | 0 | 12.4 | 2397 | 28 | 5462 | 2172 | 446 | 38 |
| none | none | 1 | 0 | 0 | 8.5 | 2111 | 36 | 4189 | 3091 | 435 | 96 |
| none | none | 5 | 0 | 0 | 7.3 | 2765 | 10 | 1751 | 3820 | 545 | 0 |

TABLE 4A-continued

| Treatment | MeSpd treatment | Exp. | Edema | Necrosis | Zn (mg/dm³) | P-amyl (U/l) | SSAT | PU | SPD | SPM | N¹AcSPD |
|---|---|---|---|---|---|---|---|---|---|---|---|
| none | none | 5 | 0 | 0 | 5.6 | 2084 | 31 | 1652 | 3557 | 558 | 55 |
| Zn 6h | none | 1 | 2 | 0 | 33.3 | 2622 | 1731 | 5361 | 364 | 298 | 124 |
| Zn 6h | none | 1 | 1 | 0 | 28.6 | 1669 | 1619 | 4863 | 378 | 348 | 98 |
| Zn 6h | none | 1 | 1 | 0 | 8.5 | 2452 | 39 | 7013 | 2938 | 483 | 69 |
| Zn 12 h | none | 1 | 2 | 1 | 42.7 | 2336 | 6709 | 6932 | 314 | 168 | 89 |
| Zn 12 h | none | 1 | 1 | 1 | 41.0 | 3937 | 5475 | 7234 | 332 | 177 | 100 |
| Zn 12 h | none | 1 | 2 | 3 | 33.9 | 4569 | 4462 | 5531 | 236 | 120 | 59 |
| Zn 12 h | none | 1 | 1 | 3 | 38.0 | 3472 | 5334 | 5858 | 278 | 134 | 68 |

TABLE 4B 24 hours after the initiation of pancreatitis.

| Treatment | MeSpd treatment | Exp. | Edema | Necr. | Zn (mg/dm³) | P-amyl (U/l) | SSAT | PU | SPD | SPM | N¹AcSpd | MeSpd |
|---|---|---|---|---|---|---|---|---|---|---|---|---|
| Zn 24 h | none | 1 | 3 | 4 | 26.3 | 13050 | 5877 | 3550 | 157 | 60 | 42 | |
| Zn 24 h | none | 1 | 1 | 4 | 28.6 | 40770 | 2444 | 3818 | 160 | 60 | 91 | |
| Zn 24 h | none | 1 | 0 | 0 | 8.1 | 2435 | 20 | 3825 | 4456 | 460 | 50 | |
| Zn 24 h | none | 1 | 2 | 4 | 32.2 | 18300 | 8870 | 3363 | 232 | 78 | 51 | |
| Zn 24 h | none | 2 | 1 | 4 | 29.8 | 22830 | 5464 | 2244 | 257 | 111 | 31 | |
| Zn 24 h | none | 2 | 2 | 4 | 38.6 | 31440 | 727 | 3770 | 219 | 113 | 53 | |
| Zn 24 h | none | 5 | 0 | 0 | 6.9 | 2108 | 9 | 1860 | 3615 | 682 | 0 | |
| Zn 24 h | none | 5 | 2 | 4 | 65.5 | 10600 | 90 | 3695 | 544 | 207 | 29 | |
| Zn 24 h | none | 5 | 0 | 0 | 8.0 | 2292 | 20 | 2547 | 3497 | 559 | 45 | |
| Zn 24 h | none | 5 | 2 | 4 | 39.7 | 9870 | 97 | 2801 | 209 | 57 | 15 | |
| Zn 24 h | 3 h/8 h | 5 | 0 | 0 | 6.5 | 2743 | 50 | 3231 | 1165 | 299 | 54 | 1943 |
| Zn 24 h | 3 h/8 h | 5 | 2 | 3 | 10.1 | 20380 | 91 | 2820 | 265 | 128 | 58 | 1425 |
| Zn 24 h | 3 h/8 h | 5 | 2 | 4 | 38.6 | 11420 | 100 | 2269 | 119 | 69 | 31 | 907 |
| Zn 24 h | 3 h/8 h | 5 | 0 | 0 | 6.2 | 2801 | 18 | 2159 | 3405 | 441 | 0 | 0 |
| Zn 24 h | 6 h/12 h | 1 | 0 | 0 | 7.0 | 2686 | 1403 | 6768 | 478 | 213 | 113 | 2268 |
| Zn 24 h | 6 h/12 h | 1 | 0 | 0 | 6.9 | 2153 | 37 | 6932 | 1114 | 431 | 45 | 3242 |
| Zn 24 h | 6 h/12 h | 1 | 1 | 0 | 6.4 | 2572 | 40 | 4915 | 1297 | 408 | 43 | 3098 |
| Zn 24 h | 6 h/12 h | 1 | 2 | 4 | 26.9 | 30970 | 10372 | 2335 | 108 | 41 | 66 | 745 |
| Zn 24 h | 6 h/12 h | 2 | 3 | 4 | 42.7 | 42250 | 3866 | 1932 | 96 | 54 | 71 | 798 |
| Zn 24 h | 6 h/12 h | 2 | 2 | 4 | 35.7 | 30860 | 5823 | 2401 | 105 | 54 | 98 | 954 |
| Zn 24 h | 6 h/12 h | 2 | 1 | 4 | 25.1 | 28400 | 6216 | 1911 | 84 | 50 | 134 | 834 |
| Zn 24 h | 6 h/12 h | 2 | 0 | 0 | 26.9 | 5110 | 1024 | 3790 | 1096 | 276 | 20 | 1993 |
| Zn 24 h | 6 h/12 h | 2 | 4 | 2 | 45.1 | 25050 | 5748 | 1935 | 100 | 46 | 59 | 728 |
| Zn 24 h | 12 h | 1 | 1 | 0 | 7.1 | 3048 | 29 | 5328 | 1360 | 479 | 16 | 1113 |
| Zn 24 h | 12 h | 1 | 2 | 4 | 43.9 | 17170 | 6855 | 3361 | 124 | 47 | 57 | 371 |
| Zn 24 h | 12 h | 1 | 3 | 4 | 37.4 | 31310 | 4852 | 2782 | 153 | 61 | 65 | 333 |
| Zn 24 h | 12 h | 1 | 2 | 3 | 41.0 | 18960 | 6866 | 3116 | 126 | 45 | 42 | 334 |

TABLE 4C 48 hours after the initiation of pancreatitis.

| Treatment | MeSpd treatment | Exp. | Edema | Necr. | Zn (mg/dm³) | P-amyl (U/l) | SSAT | PU | SPD | SPM | N¹AcSpd | MeSpd |
|---|---|---|---|---|---|---|---|---|---|---|---|---|
| Zn 48 h | none | 4 | 0 | 0 | 6.4 | 3041 | 24 | 1725 | 3045 | 361 | 84 | |
| Zn 48 h | none | 4 | 3 | 4 | 53.8 | 9140 | 67 | 3738 | 403 | 146 | 0 | |
| Zn 48 h | none | 4 | 0 | 0 | 6.8 | 2870 | 11 | 1117 | 3525 | 373 | 0 | |
| Zn 48 h | none | 5 | 1 | 4 | 25.1 | 3387 | 74 | 2678 | 1748 | 212 | 43 | |
| Zn 48 h | 3 h/8 h | 5 | 3 | 4 | 25.1 | 5867 | 92 | 1538 | 367 | 119 | 43 | 646 |
| Zn 48 h | 3 h/8 h | 5 | 2 | 4 | 26.9 | 5117 | 82 | 1268 | 313 | 90 | 21 | 1043 |
| Zn 48 h | 3 h/8 h | 5 | 3 | 4 | 30.4 | 29880 | 90 | 649 | 148 | 51 | 29 | 768 |
| Zn 48 h | 4 h/24 h | 4 | 0 | 0 | 5.7 | 1924 | 10 | 1522 | 1344 | 238 | 0 | 1066 |
| Zn 48 h | 4 h/24 h | 4 | 0 | 0 | 6.2 | 2740 | 28 | 2416 | 1052 | 254 | 0 | 2249 |
| Zn 48 h | 4 h/24 h | 4 | 1 | 0 | 6.3 | 2908 | 17 | 1960 | 1928 | 339 | 0 | 1415 |
| Zn 48 h | 4 h/24 h | 4 | 0 | 0 | 6.1 | 2591 | 8 | 1744 | 2533 | 557 | 0 | 1041 |
| Zn 48 h | 4 h/24 h | 4 | 3 | 4 | 29.8 | 3943 | 75 | 1896 | 369 | 112 | 0 | 1493 |
| Zn 48 h | 12 h/24 h | 1 | 3 | 4 | 22.8 | 86840 | 548 | 889 | 79 | 35 | 70 | 452 |
| Zn 48 h | 12 h/24 h | 1 | 0 | 0 | 7.8 | 2693 | 42 | 7496 | 1571 | 422 | 51 | 1053 |
| Zn 48 h | 12 h/24 h | 1 | 2 | 4 | 22.2 | 36470 | 4391 | 1078 | 165 | 61 | 49 | 560 |
| Zn 48 h | 12 h/24 h | 1 | 3 | 4 | 16.4 | 3382 | 2001 | 1345 | 456 | 141 | 42 | 629 |

TABLE 4D

Overall mortality to zinc induced acute pancreatitis in SSAT transgenic rats

| Zn treatment | MeSpd treatment | Number of all animals | Number of death animals | Mortality % |
|---|---|---|---|---|
| Zn 24 h | none | 12 | 2 | 17 |
| Zn 24 h | yes | 17 | 0 | 0 |
| Zn 48 h | none | 13 | 9 | 69 |
| Zn 48 h | yes | 13 | 1[a] | 8 |

[a]animal received MeSPD treatment 3 h/8 h

Example 13

Prevention of Zinc Induced Acute Pancreatitis in MT-SSAT Transgenic Rats Pretreated with bis-α-methylspermine.

MT-SSAT (UKUR30) transgenic rats received zinc (10 mg/kg i.p.) 24 h before sacrifice either alone or in the combination with Me$_2$SPM (25 mg/kg i.p.) administered twice 20 h and 4 h before zinc. There were three animals in each group. Plasma amylase activity was measured as a marker of pancreatitis. Histological samples were not scored, but general description is shown in Table 5. The data clearly indicates that Me$_2$Spm can be used for the prevention of acute pancreatitis in SSAT transgenic rats, as can MeSpd (discussed supra).

TABLE 5

Prevention of zinc induced acute pancreatitis in MT-SSAT transgenic rats pretreated with bis-α-methylspermine

| Treatment | Plasma amylase | Pancreatic histology |
|---|---|---|
| None | 3683 ± 116 | normal |
| Zn | 17573 ± 3738 | edema, vacuolization, necrosis |
| Zn + Me$_2$Spm | 2744 ± 837 | modest edema |

Example 14

Toxicity and Dosage Studies with the α-methylated Polyamine Analogues with Syngenic and UKU181 Transgenic Mice.

α-methylspermidine, Bis-α-methylspermine and α-methylspermine were administered in saline. Polyamines and their derivatives (pmoles/mg tissue wet weight) were determined with the aid of high-performance liquid chromatography as described by Hyvönene et al. (Hyvönen, T., Keinänen, T. A., Khomutov, A. R., Khomutov, R. M. and Eloranta T. O. (1992) *J. Chromatogr.* 574, 17–21). SSAT activity expressed as pmoles/mg tissue wet weight was assayed according to Bernacki et al. (Bernacki, R. J., Oberman, E. J., Seweryniak, K. E., Atwood, A., Bergeron, R. J. and Porter C., W. (1995) *Clin. Cancer Res.* 1, 847–8). α-amylase and Alanine Amino Transferase (ALAT) were determined from heparinized plasma using an analyzer system Microlab 200 from Merck and are expressed as U/dm$^3$. The data are expressed as means ±S.D. For statistical analysis, the two-tailed Student's t test was used.

No signs of toxicity were detected in mice with any of the methylated derivatives at the dosages used.

Generally speaking, toxicity is increased with spermine derivatives as compared with spermidine derivatives. At a dosage regimen of, for example, MeSpm or Me$_2$Spm at 50 mg/kg twice/24 h, a number of rats died. Relative toxicity has been shown to increase in the series putrescine, spermidine to spermine, the latter being the most toxic. It is likely to be the case with the methylated analogues as well.

TABLE 6

Plasma α-amylase and ALAT in syngenic and transgenic mice after α-methylpermidine injection.

| Group | α-amylase | ALAT |
|---|---|---|
| Sg 50 mg/kg | 266.76 ± 23.00 [+] | 17.90 ± 2.62 [++] |
| Sg 100 mg/kg | 281.81 ± 24.11 | 19.21 ± 5.88 [+] |
| Sg 150 mg/kg | 284.83 ± 26.90 | 18.33 ± 1.75 [+] |
| Sg 250 mg/kg | 287.41 ± 74.99 | 66.00 ± 41.71 |
| Sg 375 mg/kg | 654.32 ± 402.95 | 111.39 ± 88.95 |
| Sg 500 mg/kg | 370.45 ± 104.58 | 32.74 ± 9.497 |
| Tg 50 mg/kg | 341.62 ± 44.99 | 34.92 ± 3.77 |
| Tg 100 mg/kg | 302.90 ± 29.54 | 44.96 ± 7.18 |
| Tg 150 mg/kg | 275.79 ± 34.37 | 41.90 ± 10.08 |
| Tg 250 mg/kg | 389.38 ± 213.31 | 34.05 ± 14.92 |
| Tg 375 mg/kg | 314.51 ± 20.72 | 52.38 ± 10.48 |

The animals received a dose of methylspermidine, as presented in the table 7, 24 h. before sacrifice. There were four to five animals per each group. * and **, correspond to $p < 0.05$ and $p < 0.001$ respectively, as compared to the correspondent control. [+] and [++], correspond to $p < 0.05$ and $p < 0.001$ respectively, as compared to the correspondent treatment for the transgenic line.
Sg, syngenic;
Tg, transgenic.
Values are expressed as U/dm$^3$. Amylase activities in table 6 are calculated by using not corrected constant and are therefore not directly comparable to other amylase activities.

TABLE 7

Effect of the treatment with α-methylspermidine in the hepatic, pancreatic and renal SSAT activity in syngenic and metallothionein-SSAT mice.

| Group | Liver | Pancreas | Kidney |
|---|---|---|---|
| Sg Control | 0.66 ± 0.21 [++] | 1.311 ± 0.68 [++] | 0.68 ± 0.29 [++] |
| Sg 50 mg/kg | 3.74 ± 0.45 ** [++] | 6.58 ± 1.31 ** [++] | 4.98 ± 0.39 ** [++] |
| Sg 100 mg/kg | 3.77 ± 0.23 ** [++] | 7.50 ± 1.71 ** [++] | 4.61 ± 0.52 ** [++] |
| Sg 150 mg/kg | 4.16 ± 0.66 ** [++] | 6.91 ± 2.49 ** [++] | 5.05 ± 0.78 ** [+] |
| Sg 250 mg/kg | 3.75 ± 0.30 ** [++] | 12.10 ± 4.11 ** [++] | 6.45 ± 0.73 ** [++] |
| Sg 375 mg/kg | 9.52 ± 9.35 ** [++] | 18.19 ± 6.32 ** [++] | 9.40 ± 4.64 ** [++] |
| Sg 500 mg/kg | 16.06 ± 12.71 ** [++] | 26.85 ± 10.90 ** [++] | 14.67 ± 4.76 ** [++] |
| Tg Control | 12.63 ± 5.79 | 71.79 ± 30.17 | 1.80 ± 0.53 |
| Tg 50 mg/kg | 74.88 ± 22.19 ** | 179.02 ± 21.15 ** | 3.19 ± 0.42 ** |
| Tg 100 mg/kg | 74.88 ± 28.59 ** | 226.27 ± 41.42 ** | 3.13 ± 0.35 ** |

TABLE 7-continued

Effect of the treatment with α-methylspermidine in the hepatic, pancreatic and renal SSAT activity in syngenic and metallothionein-SSAT mice.

| Group | Liver | Pancreas | Kidney |
|---|---|---|---|
| Tg 150 mg/kg | 81.59 ± 28.59 ** | 183.078 ± 78.57 ** | 3.36 ± 2.19 * |
| Tg 250 mg/kg | 95.04 ± 28.05 ** | 188.45 ± 61.77 ** | 2.88 ± 0.36 ** |
| Tg 375 mg/kg | 135.53 ± 47.38 ** | 133.57 ± 37.75 ** | 3.40 ± 0.46 ** |

The animals were treated as described in the legend for Table 6. * and **, correspond to p < 0.05 and p < 0.001 respectively, as compared to the correspondent control. + and ++, correspond to p < 0.05 and p < 0.001 respectively, as compared to the correspondent treatment for the transgenic line.
Sg, syngenic;
Tg, transgenic.
The values are pmoles/10 min/mg tissue wet weight.

TABLE 8

Effect of the treatment with α-methylspermidine in the hepatic polyamine concentration in syngenic and SSAT mice.

| Group | Putrescine | $N^1$-Acetyl-spermidine | Spermidine | α-Methyl-spermidine | Spermine |
|---|---|---|---|---|---|
| Sg Control | ND | ND | 1129.15 ± 36.48 + | 98.89 ± 11.71 | 862.50 ± 58.15 ++ |
| Sg 50 mg/kg | ND | 21.45 ± 10.61 + | 1018.24 ± 257.95 + | 394.01 ± 63.94 * | 864.34 ± 90.79 ++ |
| Sg 100 mg/kg | 15.36 ± NA | 12.90 ± 3.71 ++ | 729.82 ± 102.29 * + | 461.44 ± 35.92 ** + | 892.64 ± 79.24 ++ |
| Sg 150 mg/kg | ND | 23.35 ± 12.44 ++ | 723.14 ± 115.49 * * | 504.41 ± 113.27 * + | 739.53 ± 170.40 + |
| Sg 250 mg/kg | 21.87 ± 1.5 + | 18.97 ± 10.36 + | 593.49 ± 29.69 ** + | 763.57 ± 44.75 ** ++ | 854.77 ± 108.73 ++ |
| Sg 375 mg/kg | 29.37 ± 0.66 + | 31.64 ± 34.78 + | 370.29 ± 170.21 ** | 1095.59 ± 222.96 ** | 644.88 ± 183.36 + |
| Sg 500 mg/kg | 119.33 ± 162.75 | 133.00 ± 183.90 | 273.13 ± 106.74 ** | 1801.46 ± 745.90 * | 666.13 ± 188.21 |
| Tg Control | 645.37 ± 131.90 | 158.70 ± 52.10 | 935.64 ± 113.63 | 134.66 ± 27.30 | 107.86 ± 26.93 |
| Tg 50 mg/kg | 1055.38 ± 184.72 * | 245.16 ± 84.81 | 329.57 ± 106.08 ** | 582.62 ± 745.90 * | 103.26 ± 188.21 |
| Tg 100 mg/kg | 834.88 ± 168.34 | 293.66 ± 18.66 * | 286.11 ± 215.27 * | 676.44 ± 100.51 ** | 97.52 ± 52.21 |
| Tg 150 mg/kg | 603.18 ± 141.87 | 230.96 ± 34.00 | 260.13 ± 162.01 * | 1206.94 ± 207.66 * | 79.41 ± 25.11 |
| Tg 250 mg/kg | 444.97 ± 163.93 | 211.54 ± 72.76 | 199.53 ± 100.74 ** | 1293.76 ± 90.02 ** | 36.38 ± 9.89 * |
| Tg 375 mg/kg | 861.39 ± 514.89 | 252.33 ± 107.93 | 168.25 ± 10.85 * | 1012.46 ± 292.84 * | 41.95 ± 8.02 * |

The animals were treated as described in the legend for Table 6.
* and **, correspond to p < 0.05 and p < 0.001 respectively, as compared to the correspondent control.
+ and ++, correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

TABLE 9

Effect of the treatment with α-methylspermidine in the pancreatic polyamine concentration in syngenic and metallothionein-SSAT mice.

| Group | Putrescine | $N^1$-Acetyl-spermidine | Spermidine | α-Methyl-spermidine | Spermine |
|---|---|---|---|---|---|
| Sg Control | 28.12 ± 7.71 + | ND | 3581.41 ± 255.44 ++ | ND | 647.80 ± 80.56 + |
| Sg 50 mg/kg | 2.82 ± NA | ND | 6597.75 ± 1034.98 * + | ND | 911.15 ± 144.75 * ++ |
| Sg 100 mg/kg | ND | 66.33 ± NA | 6089.81 ± 1039.94 * ++ | ND | 815.33 ± 179.39 + |
| Sg 150 mg/kg | 1.66 ± NA | ND | 6345.88 ± 1026.88 * ++ | ND | 833.73 ± 52.55 * ++ |
| Sg 250 mg/kg | 158.82 ± 214.86 ++ | ND | 4773.64 ± 838.69 ++ | 1363.02 ± 287.09 | 762.743 ± 110.04 ++ |
| Sg 375 mg/kg | 726.66 ± 463.77 ++ | 14.02 ± NA | 4073.3 ± 670.46++ | 1319.14 ± 203.16 | 740.93 ± 106.47 ++ |
| Sg 500 mg/kg | 812.54 ± 192.52 * | 10.62 ± 0.30 | 3669.36 ± 1235.66 | 1273.3 ± 496.76 | 652.17 ± 162.58 |
| Tg Control | 4729.52 ± 1140.80 | 89.15 ± 26.67 | 1998.75 ± 759.53 | ND | 220.86 ± 70.16 |
| Tg 50 mg/kg | 4968.25 ± 378.68 ** | 204.43 ± 64.83 | 1316.94 ± 248.44 | 627.87 ± 63.96 | 224.17 ± 46.52 |
| Tg 100 mg/kg | 4467.46 ± 412.78 ** | 656.51 ± 305.44 * | 1539.88 ± 351.44 * | 731.63 ± 119.3 | 211.73 ± 20.86 |
| Tg 150 mg/kg | 4457.91 ± 369.12 ** | 185.50 ± 102.95 | 1244.49 ± 565.07 | 942.74 ± 238.98 | 213.86 ± 76.67 |
| Tg 250 mg/kg | 4637.87 ± 211.46 ** | 137.01 ± 94.51 | 967.83 ± 396.04 | 1166.56 ± 185.72 | 157.23 ± 79.67 |
| Tg 375 mg/kg | 4826.59 ± 190.58 ** | 95.41 ± 21.13 | 1002.33 ± 365.29 | 1378.62 ± 156.1 | 122.49 ± 27.52 * |

The animals were treated as described in the legend for Table 6.
* and **, correspond to p < 0.05 and p < 0.001 respectively, as compared to the correspondent control.
+ and ++, correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

TABLE 10

Effect of the treatment with α-methylspermidine in the renal polyamine concentration in syngenic and metallothionein-SSAT mice.

| Group | Putrescine | N¹-Acetylspermidine | Spermidine | α-Methylspermidine | Spermine |
|---|---|---|---|---|---|
| Sg Control | 75.39 ± 15.75 + | ND | 230.84 ± 13.44 + | ND | 605.74 ± 59.04 |
| Sg 50 mg/kg | 45.91 ± 10.85 * + | 36.67 ± 4.02 | 315.36 ± 46.18 * + | 122.64 ± 17.56 | 856.32 ± 68.27 * |
| Sg 100 mg/kg | 68.97 ± 12.2 + | 38.89 ± 8.18 | 231.78 ± 25.15 | 146.37 ± 24.18 | 686.21 ± 75.94 + |
| Sg 150 mg/kg | 65.28 ± 13.08 + | 24.61 ± 9.43 + | 240.59 ± 28.71 | 175.49 ± 21.57 | 635.17 ± 42.35 |
| Sg 250 mg/kg | 41.84 ± 9.56 * + | 31.10 ± 12.01 + | 225.57 ± 29.21 + | 288.30 ± 50.71 + | 518.89 ± 36.68 * |
| Sg 375 mg/kg | 58.59 ± 60.04 | 27.40 ± 9.60 + | 189.46 ± 0.98 * | 477.31 ± 243.63 + | 454.49 ± 64.44 * + |
| Sg 500 mg/kg | 789.63 ± 1488.65 | 46.34 ± 22.74 | 181.32 ± 28.81 * | 1078.16 ± 593.18 | 458.07 ± 107.68 |
| Tg Control | 160.29 ± 21.31 | 22.87 ± 2.77 | 191.14 ± 15.58 | ND | 599.97 ± 56.66 |
| Tg 50 mg/kg | 179.10 ± 83.7 | 49.14 ± 14.69 | 231.02 ± 15.59 * | 133.67 ± 14.33 | 896.89 ± 25.61 ** |
| Tg 100 mg/kg | 133.86 ± 47.03 | 65.00 ± 26.62 | 212.40 ± 10.9 | 136.61 ± 16.3 | 840.58 ± 67.32 * |
| Tg 150 mg/kg | 119.47 ± 19.65 * | 41.78 ± 9.18 * | 201.24 ± 19.1 | 148.99 ± 46.15 | 721.39 ± 64.84 * |
| Tg 250 mg/kg | 103.63 ± 24.75 * | 48.47 ± 4.90 * | 185.82 ± 18.56 | 169.73 ± 14.98 | 597.01 ± 91.36 |
| Tg 375 mg/kg | 127.41 ± 30.56 | 44.65 ± 10.38 | 173.73 ± 13.69 | 192.90 ± 16.39 | 580.26 ± 51.87 |

The animals were treated as described in the legend for Table 6.
* and **, correspond to $p < 0.05$ and $p < 0.001$ respectively, as compared to the correspondent control.
+ and ++, correspond to $p < 0.05$ and $p < 0.001$ respectively, as compared to the correspondent treatment for the transgenic line.
Sg, syngenic;
Tg, transgenic;
NA, non-applicable;
ND, not detected.
Values are pmoles/mg tissue wet weight.

TABLE 11

Plasma α-amylase and ALAT in syngenic and transgenic mice after Bis-α-methylspermine injection.

| Group | α-amylase | ALAT |
|---|---|---|
| Sg Control | 3466.33 ± 249.86 + | 52.00 ± 8.72 |
| Sg 12.5 mg/kg | 3167.33 ± 85.99 | 49.33 ± 8.50 |
| Sg 25 mg/kg | 2931.00 ± 239.29 | 57.67 ± 15.89 |
| Sg 37.5 mg/kg | 2827.00 ± 121.50 * | 35.67 ± 3.21 * |
| Sg 50 mg/kg | 2715.33 ± 525.00 | 62.00 ± 25.46 |
| Tg Control | 2640.33 ± 249.87 | 56.67 ± 9.45 |
| Tg 12.5 mg/kg | 2822.67 ± 431.32 | 50.67 ± 10.07 |
| Tg 25 mg/kg | 3242.33 ± 205.44 * | 45.33 ± 21.39 |
| Tg 37.5 mg/kg | 2540.00 ± 423.44 | 31.00 ± 1.41 * |
| Tg 50 mg/kg | 2886.00 ± 519.63 | 60.00 ± 29.46 |

The animals received a dose of bis-α-methylspermine, as presented in the table 12, 24 h. before sacrifice. There were three to five animals per group. * and **, correspond to $p < 0.05$ and $p < 0.001$ respectively, as compared to the correspondent control. + and ++, correspond to $p < 0.05$ and $p < 0.001$ respectively, as compared to the correspondent treatment for the transgenic line.
Sg, syngenic;
Tg, transgenic.
Values are expressed as $U/dm^3$.

TABLE 12

Effect of the treatment with Bis-α-methylspermine in the hepatic, pancreatic and renal SSAT activity in syngenic and metallothionein-SSAT mice.

| Group | Liver | Pancreas | Kidney |
|---|---|---|---|
| Sg Control | 0.66 ± 0.21 ++ | 1.31 ± 0.68 ++ | 0.68 ± 0.29 ++ |
| Sg 12.5 mg/kg | ND | 3.38 ± 1.49 ** ++ | 0.32 ± 0.14 * ++ |
| Sg 25 mg/kg | ND | 4.23 ± 0.97 ** ++ | 0.58 ± 0.43 + |
| Sg 37.5 mg/kg | ND | 3.18 ± 1.00 ** ++ | 0.33 ± 0.14 * + |
| Sg 50 mg/kg | ND | 8.44 ± 4.54 ** ++ | 0.60 ± 0.19 + |
| Tg Control | 12.63 ± 5.79 | 71.79 ± 30.17 | 1.80 ± 0.53 |
| Tg 12.5 mg/kg | 6.56 ± 2.79 * | 34.11 ± 10.55 * | 0.72 ± 0.24 ** |
| Tg 25 mg/kg | 9.08 ± 1.56 | 65.20 ± 13.34 | 1.48 ± 0.92 |

TABLE 12-continued

Effect of the treatment with Bis-α-methylspermine in the hepatic, pancreatic and renal SSAT activity in syngenic and metallothionein-SSAT mice.

| Group | Liver | Pancreas | Kidney |
|---|---|---|---|
| Tg 37.5 mg/kg | 55.79 ± 55.16 * | 124.95 ± 59.41 * | 8.04 ± 14.36 |
| Tg 50 mg/kg | 13.11 ± 2.51 | 62.05 ± 24.83 | 1.24 ± 0.39 * |

The animals were treated as described in the legend for Table 11. * and **, correspond to $p < 0.05$ and $p < 0.001$ respectively, as compared to the correspondent control. + and ++, correspond to $p < 0.05$ and $p < 0.001$ respectively, as compared to the correspondent treatment for the transgenic line.
Sg, syngenic;
Tg, transgenic;
ND, not detected.
Values are expressed as pmoles/10 min/ tissue wet weight.

TABLE 13

Effect of the treatment with bis-α-methylspermidine in the hepatic polyamine concentration in syngenic and metallothionein-SSAT mice.

| Group | Putrescine | $N^1$-Acetyl-spermidine | $N^8$-Acetyl-spermidine | Spermidine | Spermine | Bis-α-Methylspermine |
|---|---|---|---|---|---|---|
| Sg Control | ND | ND | ND | 1129.15 ± 36.48 + | 862.50 ± 58.15 ++ | ND |
| Sg 12.5 mg/kg | 92.42 ± 26.21 + | ND | 0.75 ± NA | 927.28 ± 61.14 * | 708.04 ± 46.08 * ++ | 159.88 ± 24.85 + |
| Sg 25 mg/kg | 73.69 ± 41.46 + | ND | 2.38 ± 3.59 | 879.17 ± 134.03 * | 699.86 ± 56.27 * ++ | 317.22 ± 66.16 + |
| Sg 37.5 mg/kg | 96.27 ± 31.84 + | 14.57 ± NA | 2.10 ± 2.95 + | 772.68 ± 93.22 * + | 754.59 ± 147.49 + | 283.40 ± 36.38 |
| Sg 50 mg/kg | 52.40 ± NA | ND | 8.72 ± 3.72 | 688.44 ± 75.13 ** + | 687.71 ± 46.60 * ++ | 379.77 ± 81.34 |
| Tg Control | 645.37 ± 131.90 | 158.70 ± 52.10 | 23.78 ± 4.38 | 935.64 ± 113.63 | 107.855 ± 26.93 | ND |
| Tg 12.5 mg/kg | 944.38 ± 223.94 | 226.74 ± 46.50 | 9.43 ± 5.93 * | 792.81 ± 314.10 | 104.48 ± 18.22 | 29.55 ± 40.05 |
| Tg 25 mg/kg | 895.27 ± 193.78 | 219.53 ± 19.54 | 9.03 ± 5.24 * | 673.04 ± 284.45 | 66.74 ± 15.96 | 105.83 ± 12.98 |
| Tg 37.5 mg/kg | 1032.66 ± 446.20 | 355.10 ± 62.94 | 19.03 ± 6.84 | 404.05 ± 291.34 * | 74.10 ± 17.52 | 158.82 ± 168.55 |
| Tg 50 mg/kg | 717.95 ± 71.88 | 207.30 ± 64.85 | 19.27 ± 6.11 | 293.21 ± 43.58 ** | 69.63 ± 16.46 | 300.81 ± 26.31 |

α-Methylspermidine was not detected in the liver of bis-α-methylspermine treated mice. The animals were treated as described in the legend for Table 11.
* and **, correspond to $p < 0.05$ and $p < 0.001$ respectively, as compared to the correspondent control.
+ and ++, correspond to $p < 0.05$ and $p < 0.001$ respectively, as compared to the correspondent treatment for the transgenic line.
Sg, syngenic;
Tg, transgenic;
NA, non-applicable;
ND, not detected.
Values are pmoles/mg tissue wet weight.

TABLE 14

Effect of the treatment with bis-α-methylspermine in the pancreatic polyamine concentration in syngenic and metallothionein-SSAT mice.

| Group | Putrescine | $N^1$-Acetyl-spermidine | $N^8$-Acetyl-spermidine | Spermidine | Spermine | Bis-α-Methyl-spermine |
|---|---|---|---|---|---|---|
| Sg Control | 28.12 ± 7.71 + | ND | ND | 3581.41 ± 255.44 + | 647.80 ± 80.56 + | ND |
| Sg 12.5 mg/kg | 298.55 ± 75.14 *+ | ND | 60.41 ± NA | 6575.15 ± 614.21 * + | 981.28 ± 201.81 + | 259.30 ± 10.04 |
| Sg 25 mg/kg | 467.21 ± 419.85+ | ND | ND | 5733.90 ± 300.80 ** + | 528.55 ± 241.57 + | 343.17 ± 35.11 |
| Sg 37.5 mg/kg | 233.06 ± 45.81 *+ | 123.67 ± NA | 55.34 ± NA | 5997.63 ± 24.26 ** + | 708.66 ± 179.23 ++ | 415.40 ± 92.86 |
| Sg 50 mg/kg | 297.48 ± 123.94++ | ND | 82.23 ± NA | 5613.06 ± 608.55 * ++ | 561.50 ± 77.66 ++ | 459.26 ± 18.65 |
| Tg Control | 4729.52 ± 1140.80 | 89.15 ± 26.67 | ND | 1998.75 ± 759.53 | 220.86 ± 70.16 | ND |
| Tg 12.5 mg/kg | 6168.51 ± 1253.00 | 267.28 ± 20.18 ** | 0.08 | 3646.27 ± 367.99 | 187.07 ± 5.15 | ND |
| Tg 25 mg/kg | 7573.46 ± 1084.90 * | 474.31 ± 140.09 * | 64.06 ± 0.08 | 3389.87 ± 447.32 | 73.43 ± 6.82 * | 315.13 ± 82.18 |
| Tg 37.5 mg/kg | 8158.57 ± 2876.94 | 339.96 ± 171.83 * | 90.85 ± NA | 2268.60 ± 1821.72 * | 98.77 ± 82.83 | 421.62 ± 147.44 |
| Tg 50 mg/kg | 5123.85 ± 573.32 | 288.51 ± 187.26 | ND | 2326.21 ± 126.42 | 119.48 ± 37.92 | 400.64 ± 63.85 |

α-Methylspermidine was not detected in the pancreas of bis-α-methylspermine treated mice. The animals were treated as described in the legend for Table 11.
* and **, correspond to $p < 0.05$ and $p < 0.001$ respectively, as compared to the correspondent control.
+ and ++, correspond to $p < 0.05$ and $p < 0.001$ respectively, as compared to the correspondent treatment for the transgenic line.
Sg, syngenic;
Tg, transgenic;
NA, non-applicable;
ND, not detected.
Values are pmoles/mg tissue wet weight.

TABLE 15

Effect of the treatment with bis-α-methylspermine in the renal polyamine concentration in syngenic and metallothionein-SSAT mice.

| Group | Putrescine | $N^1$-Acetyl-spermidine | $N^8$-Acetyl-spermidine | Spermidine | Spermine | Bis-α-Methylspermine |
|---|---|---|---|---|---|---|
| Sg Control | 75.39 ± 15.75 [+] | ND | 13.19 ± 3.44 | 230.84 ± 13.44 [+] | 605.74 ± 59.04 | ND |
| Sg 12.5 mg/kg | 142.47 ± 102.93 | 33.17 ± NA | 17.62 ± 6.43 | 246.29 ± 56.26 * | 456.65 ± 7.52 * [++] | 259.30 ± 10.04 |
| Sg 25 mg/kg | 87.46 ± 9.17 [+] | 28.39 ± 2.60 | 17.70 ± 10.63 | 257.13 ± 42.29 * | 459.99 ± 49.44 * | 343.17 ± 35.11 |
| Sg 37.5 mg/kg | 93.95 ± 21.61 | 28.73 ± 8.41 | 15.95 ± 6.92 | 289.83 ± 26.46 ** [+] | 513.58 ± 20.97 | 415.40 ± 92.86 |
| Sg 50 mg/kg | 98.32 ± 42.84 [+] | ND | 21.07 ± 5.81 | 248.63 ± 72.04 * | 424.06 ± 73.64 * | 459.26 ± 18.65 |
| Tg Control | 160.29 ± 21.31 | ND | 15.73 ± 3.57 | 191.14 ± 15.58 | 599.97 ± 56.66 | ND |
| Tg 12.5 mg/kg | 184.32 ± 71.46 | 19.74 ± NA | 16.35 ± 1.03 | 235.80 ± 2.12 * | 739.17 ± 43.60 * | ND |
| Tg 25 mg/kg | 137.26 ± 20.14 | 25.57 ± NA | 17.52 ± 3.88 | 216.59 ± 31.25 | 565.06 ± 44.32 | 315.13 ± 82.18 |
| Tg 37.5 mg/kg | 225.66 ± 94.33 | 27.37 ± 10.49 | 16.82 ± 4.23 | 185.57 ± 7.49 | 426.59 ± 49.98 * | 421.62 ± 147.44 |
| Tg 50 mg/kg | 173.97 ± 11.76 | ND | 12.21 ± 4.20 | 204.20 ± 24.49 | 481.68 ± 32.14 * | 400.64 ± 63.85 |

α-Methylspermidine was not detected in the kidney of bis-α-methylspermine treated mice. The animals were treated as described in the legend for Table 11.
* and **, correspond to p < 0.05 and p < 0.001 respectively, as compared to the correspondent control.
[+] and [++], correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

TABLE 16

Plasma α-amylase and ALAT in syngenic and transgenic mice after α-methylspermine injection.

| Group | α-amylase | ALAT |
|---|---|---|
| Sg Control | 3466.33 ± 249.86 [+] | 52.00 ± 8.72 |
| Sg 12.5 mg/kg | 2352.00 ± 206.37 * | 54.33 ± 4.16 |
| Sg 25 mg/kg | 2645.67 ± 161.87 * [+] | 43.67 ± 4.04 |
| Sg 37.5 mg/kg | 2610.67 ± 144.67 * | 47.67 ± 13.43 |
| Sg 50 mg/kg | 2512.33 ± 275.71 * | 49.00 ± 2.83 |
| Tg Control | 2640.33 ± 249.87 | 56.67 ± 9.45 |
| Tg 12.5 mg/kg | 2675.67 ± 305.64 | 58.67 ± 7.77 |
| Tg 25 mg/kg | 2044.67 ± 112.93 * | 44.67 ± 5.69 |
| Tg 37.5 mg/kg | 2450.00 ± 410.12 | 37.00 ± 2.83 |
| Tg 50 mg/kg | 2667.00 ± 297.24 | 41.33 ± 3.79 |

The animals received a dose of α-methylspermine, as presented in the table 17, 24 h. before sacrifice. There were three animals per group. * and **, correspond to p < 0.05 and p < 0.001 respectively, as compared to the correspondent control. [+] and [++], correspond to p < 0.05 and p < 0.001 respectively, as compared to the correspondent treatment for the transgenic line.
Sg, syngenic;
Tg, transgenic.
Values are expressed as U/dm$^3$.

TABLE 17

Effect of the treatment with α-methylspermine in the hepatic, pancreatic and renal SSAT activity in syngenic and metallothionein-SSAT mice.

| Group | Liver | Pancreas | Kidney |
|---|---|---|---|
| Sg Control | 0.661 ± 0.21 [++] | 1.311 ± 0.69 [++] | 0.68 ± 0.29 [++] |
| Sg 12.5 mg/kg | 0.47 ± 0.24 [++] | 2.03 ± 1.26 [++] | 3.65 ± 2.39 * [+] |
| Sg 25 mg/kg | 0.26 ± 0.21 ** [++] | 1.72 ± 0.50 [++] | 2.76 ± 2.52 * |
| Sg 37.5 mg/kg | 0.75 ± 0.68 [++] | 1.46 ± 0.93 [++] | 4.29 ± 2.38 ** |
| Sg 50 mg/kg | 0.52 ± 0.25 [++] | 2.23 ± 1.21 * [++] | 3.20 ± 2.40 * |
| Tg Control | 12.63 ± 5.79 | 71.79 ± 30.17 | 1.80 ± 0.53 |
| Tg 12.5 mg/kg | 21.19 ± 10.98 * | 609.10 ± 399.64 ** | 5.86 ± 1.91 ** |
| Tg 25 mg/kg | 30.81 ± 17.87 * | 561.36 ± 235.38 ** | 3.06 ± 2.23 |
| Tg 37.5 mg/kg | 24.88 ± 1.91 ** | 543.84 ± 183.48 ** | 3.47 ± 2.52 * |
| Tg 50 mg/kg | 39.44 ± 11.27 ** | 707.60 ± 120.21 ** | 2.95 ± 1.82 |

The animals were treated as described in the legend for Table 16. * and **, correspond to p < 0.05 and p < 0.001 respectively, as compared to the correspondent control. [+] and [++], correspond to p < 0.05 and p < 0.001 respectively, as compared to the correspondent treatment for the transgenic line.
Sg, syngenic;
Tg, transgenic.
Values are expressed as pmoles/10 min/ tissue wet weight.

TABLE 18

Effect of the treatment with α-methylspermine in the hepatic polyamine concentration in syngenic and metallothionein-SSAT mice.

| Group | Putrescine | $N^1$-Acetyl-spermidine | $N^8$-Acetyl-spermidine | Spermidine | α-Methyl-spermidine | Spermine | α-Methyl-spermine |
|---|---|---|---|---|---|---|---|
| Sg Control | ND | ND | ND | 1129.15 ± 36.48 + | ND | 862.50 ± 58.15 ++ | ND |
| Sg 12.5 mg/kg | 39.46 ± NA | 37.49 ± 1.03 + | ND | 669.94 ± 544.07 | ND | 568.21 ± 57.25 * ++ | 470.60 ± 64.69 + |
| Sg 25 mg/kg | 44.18 ± 1.53 + | ND | ND | 1015.51 ± 203.06 + | ND | 411.06 ± 65.92 ** + | 420.20 ± 57.62 + |
| Sg 37.5 mg/kg | ND | ND | ND | 830.89 ± 52.97 * ++ | ND | 485.75 ± 24.19 ** ++ | 510.72 ± 35.16 ++ |
| Sg 50 mg/kg | 22.71 ± NA | 45.74 ± NA | 15.33 ± NA | 780.24 ± 85.62 * ++ | ND | 419.39 ± 59.52 ** ++ | 521.41 ± 87.53 + |
| Tg Control | 645.37 ± 131.90 | 158.70 ± 52.10 | 23.78 ± 4.38 | 935.64 ± 113.63 | ND | 107.855 ± 26.93 | ND |
| Tg 12.5 mg/kg | 857.28 ± 150.15 | 242.81 ± 82.39 | ND | 717.42 ± 419.34 | ND | 62.74 ± 13.62 | 138.89 ± 22.47 |
| Tg 25 mg/kg | 872.47 ± 150.44 | 317.98 ± 140.33 | 36.49 ± NA | 349.61 ± 150.36 * | 197.89 ± 47.51 | 49.71 ± 9.31* | 145.99 ± 15.83 |
| Tg 37.5 mg/kg | 774.33 ± 170.89 | 180.48 ± 16.95 | 14.15 ± 1.12 | 305.70 ± 87.70 * | 274.07 ± 18.43 | 47.47 ± 11.47 * | 203.75 ± 27.39 |
| Tg 50 mg/kg | 1057.25 ± 134.08 * | 265.90 ± 43.26 | ND | 196.67 ± 53.06 ** | 255.30 ± 60.90 | 38.02 ± 17.45 * | 168.36 ± 13.24 |

The animals were treated as described in the legend for Table 16.
* and **, correspond to p < 0.05 and p < 0.001 respectively, as compared to the correspondent control.
+ and ++, correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

TABLE 19

Effect of the treatment with α-methylspermine in the pancreatic polyamine concentration in syngenic and metallothionein-SSAT mice.

| Group | Putrescine | $N^1$-Acetyl-spermidine | $N^8$-Acetyl-spermidine | Spermidine | Spermine | α-Methyl-spermine |
|---|---|---|---|---|---|---|
| Sg Control | 28.12 ± 7.71 + | ND | ND | 3581.41 ± 255.44 + | 647.80 ± 80.56 + | ND |
| Sg 12.5 mg/kg | 80.74 ± 65.72 + | 56.32 ± NA | 17.17 ± 2.68 | 7952.04 ± 3026.02 * + | 1048.44 ± 396.24 + | ND |
| Sg 25 mg/kg | 50.98 ± 21.45 + | 19.45 ± NA | 24.47 ± 8.15 | 5421.66 ± 725.78 * + | 729.10 ± 104.47 + | ND |
| Sg 37.5 mg/kg | 36.15 ± 13.42 + | ND | ND | 5806.20 ± 1051.30 * + | 804.72 ± 169.17 + | ND |
| Sg 50 mg/kg | 107.70 ± 32.53 * | ND | 19.89 ± NA | 6839.92 ± 1614.00 * | 811.45 ± 363.76 | ND |
| Tg Control | 4729.52 ± 1140.80 | 89.15 ± 26.67 | ND | 1998.75 ± 759.53 | 220.86 ± 70.16 | ND |
| Tg 12.5 mg/kg | 5691.31 ± 942.07 | 154.67 ± 151.30 | ND | 2304.42 ± 622.75 * | 42.35 ± 24.53 * | 132.85 ± 26.34 |
| Tg 25 mg/kg | 5798.24 ± 1421.46 | 327.88 ± 313.23 | ND | 2449.50 ± 375.53 | 37.63 ± 7.76 * | 130.62 ± 33.84 |
| Tg 37.5 mg/kg | 7426.10 ± 851.66 * | 176.49 ± 67.68 | ND | 2106.09 ± 561.49 * | 51.89 ± 44.56 * | 105.85 ± 91.76 |
| Tg 50 mg/kg | 9027.03 ± 4249.28 | 284.83 ± 37.00 * | ND | 3570.11 ± 1251.82 | 70.53 ± 19.79 * | 185.90 ± 20.82 |

α-Methylspermidine was not detected in the pancreas of methylspermine treated mice. The animals were treated as described in the legend for Table 16.
* and **, correspond to p < 0.05 and p < 0.001 respectively, as compared to the correspondent control.
+ and ++, correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

TABLE 20

Effect of the treatment with α-methylspermine in the renal polyamine concentration in syngenic and metallothionein-SSAT mice.

| Group | Putrescine | $N^1$-Acetyl-spermidine | $N^8$-Acetyl-spermidine | Spermidine | Spermine | α-Methyl-spermine |
|---|---|---|---|---|---|---|
| Sg Control | 75.39 ± 15.75 + | 30.08 ± NA | 13.19 ± 3.44 | 230.84 ± 13.44 + | 605.74 ± 59.04 | ND |
| Sg 12.5 mg/kg | 48.17 ± 2.01 | 46.16 ± 18.04 | 24.91 ± 1.85 * | 312.55 ± 54.73 * | 247.41 ± 17.76 ** | 197.48 ± 6.80 |
| Sg 25 mg/kg | 122.64 ± 76.39 | 59.48 ± 8.28 | 25.80 ± 4.69 * | 215.41 ± 24.53 * + | 272.18 ± 41.37 * | 228.87 ± 6.44 |
| Sg 37.5 mg/kg | 59.01 ± 33.38 | 30.29 ± 2.27 | 24.30 ± 2.35 * | 244.82 ± 57.60 * | 207.72 ± 22.35 ** | 245.67 ± 38.85 |
| Sg 50 mg/kg | 160.04 ± 30.57 * + | 48.23 ± 8.34 | 21.09 ± 4.73 | 193.19 ± 32.95 * | 258.42 ± 16.45 ** + | 263.69 ± 49.92 |
| Tg Control | 160.29 ± 21.31 | 22.87 ± 2.77 | 15.73 ± 3.57 | 191.14 ± 15.58 | 599.97 ± 56.66 | ND |

TABLE 20-continued

Effect of the treatment with α-methylspermine in the renal polyamine concentration in syngenic and metallothionein-SSAT mice.

| Group | Putrescine | $N^1$-Acetyl-spermidine | $N^8$-Acetyl-spermidine | Spermidine | Spermine | α-Methyl-spermine |
|---|---|---|---|---|---|---|
| Tg 12.5 mg/kg | 58.16 ± 23.62 * | 38.55 ± 6.22 * | 24.62 ± 3.24 | 247.60 ± 56.67 | 208.03 ± 35.62 ** | 198.34 ± 10.11 |
| Tg 25 mg/kg | 68.39 ± 12.00 * | 42.95 ± NA | 25.16 ± 5.34 | 156.66 ± 15.84 | 209.57 ± 20.03 ** | 227.76 ± 11.79 |
| Tg 37.5 mg/kg | 95.60 ± 73.47 | 32.33 ± 12.95 | 24.59 ± 7.13 | 233.85 ± 49.48 | 158.91 ± 42.08 ** | 224.06 ± 27.10 |
| Tg 50 mg/kg | 91.94 ± 11.02 * | 44.20 ± 6.90 * | 24.48 ± 5.62 | 155.85 ± 28.19 | 205.04 ± 11.19 ** | 319.33 ± 19.28 |

α-Methylspermidine was not detected in the kidney of methylspermine treated mice. The animals were treated as described in the legend for Table 16.
* and **, correspond to p < 0.05 and p < 0.001 respectively, as compared to the correspondent control.
+ and ++, correspond to p < 0.05 and p < 0.001 respectively, as compared to the correspondent treatment for the transgenic line.
Sg, syngenic;
Tg, transgenic;
NA, non-applicable;
ND, not detected.
Values are pmoles/mg tissue wet weight.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method of treating pancreatitis comprising administering to a patient a compound of formula (I):

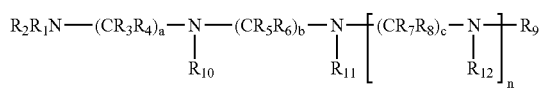

wherein: each of a, b and c is an integer from 2 to about 6; n is an integer 0 or 1; and each of $R_1$, $R_2$, $R_3$, $R_4$, $R_5$, $R_6$, $R_7$, $R_8$, $R_9$, $R_{10}$, $R_{11}$ and $R_{12}$ are, independently, hydrogen or alkyl of 1 to about 6 carbons; with the proviso that when n is 0, at least one of $R_3$, $R_4$, $R_5$, and $R_6$ is alkyl of 1 to about 6 carbons, and when n is 1, at least one of $R_3$, $R_4$, $R_5$, $R_6$, $R_7$ and $R_8$ is alkyl of 1 to about 6 carbons, wherein said compound is administered to said patient in an effective amount to treat pancreatitis.

2. A method according to claim 1 wherein a is 3, b is 4, and n is 0.

3. A method according to claim 2 wherein each of $R_3$, $R_4$, $R_5$, and $R_6$ is, independently, hydrogen or methyl.

4. A method according to claim 3 wherein the compound of formula I has the formula

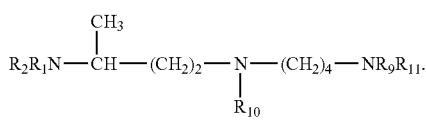

5. A method according to claim 4 wherein each of $R_1$, $R_2$, $R_9$, $R_{10}$ and $R_{11}$ is hydrogen.

6. A method according to claim 5 wherein the compound of formula I has the formula

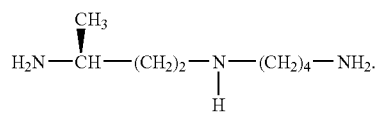

7. A method according to claim 5 wherein the compound of formula I has the formula

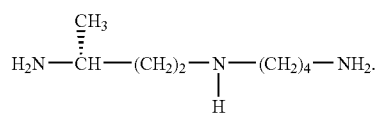

8. A method according to claim 1 wherein a is 3, b is 4, c is 3, and n is 1.

9. A method according to claim 8 wherein each of $R_3$, $R_4$, $R_5$, $R_6$, $R_7$ and $R_8$ is, independently, hydrogen or methyl.

10. A method according to claim 9 wherein the compound of formula I has the formula

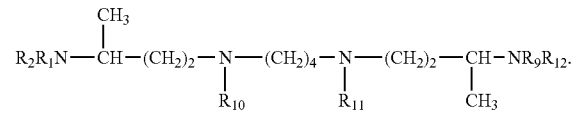

11. A method according to claim 10 wherein each of $R_1$, $R_2$, $R_9$, $R_{10}$, $R_{11}$ and $R_{12}$ is hydrogen.

12. A method according to claim 9 wherein the compound of formula I has the formula

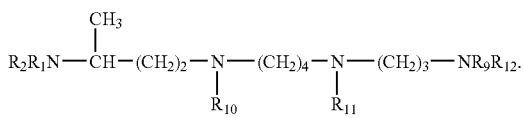

13. A method according to claim 12 wherein each of $R_1$, $R_2$, $R_9$, $R_{10}$, $R_{11}$ and $R_{12}$ is hydrogen.

14. A method of treating pancreatitis comprising administering to a patient an alkylated analog of spermidine selected from the group consisting of methylspermidine, 1-methylspermidine, α-methylspermidine, and $N^1$-acetylspermidine in an effective amount to treat pancreatitis.

* * * * *